(12) United States Patent
Bolskar et al.

(10) Patent No.: US 7,671,230 B2
(45) Date of Patent: Mar. 2, 2010

(54) DERIVATIZATION AND SOLUBILIZATION OF INSOLUBLE CLASSES OF FULLERENES

(75) Inventors: Robert D. Bolskar, Boulder, CO (US); J. Michael Alford, Lakewood, CO (US)

(73) Assignee: TDA Research, Inc., Wheat Ridge, CO (US)

(*) Notice: Subject to any disclaimer, the term of this patent is extended or adjusted under 35 U.S.C. 154(b) by 1175 days.

(21) Appl. No.: 10/263,375

(22) Filed: Oct. 1, 2002

(65) Prior Publication Data

US 2003/0065206 A1 Apr. 3, 2003

Related U.S. Application Data

(60) Provisional application No. 60/326,353, filed on Oct. 1, 2001, provisional application No. 60/371,380, filed on Apr. 9, 2002.

(51) Int. Cl.
*C07C 69/76* (2006.01)
*C07C 233/00* (2006.01)
*C07F 9/02* (2006.01)

(52) U.S. Cl. .................. 560/82; 977/734; 977/735; 977/737; 558/87; 564/161

(58) Field of Classification Search .................. 558/87, 558/357; 560/8, 82; 564/161; 977/734, 977/735, 737
See application file for complete search history.

(56) References Cited

U.S. PATENT DOCUMENTS

| | | | |
|---|---|---|---|
| 5,475,172 A | 12/1995 | Cahill et al. | 585/27 |
| 5,503,643 A | 4/1996 | Schriver et al. | 44/282 |
| 5,587,476 A | 12/1996 | Kampe et al. | 540/472 |

(Continued)

FOREIGN PATENT DOCUMENTS

EP 00695287 A1 2/1996

(Continued)

OTHER PUBLICATIONS

Woods et al., Higher Adducts of C60 by Tether-directed Remote functionalization, Angewandte Chemie, international, Ed., Nov. 5, 2000, 39, p. 3813-3816.*

(Continued)

*Primary Examiner*—Taylor Victor Oh
(74) *Attorney, Agent, or Firm*—Greenlee, Winner and Sullivan, P.C.

(57) ABSTRACT

This invention provides improved methods for the derivatization and solubilization of fullerenes, which are particularly useful for those fullerenes that are normally insoluble and which are specifically applied, among others, to endohedral fullerenes, including endohedral metallofullerenes; empty fullerenes, including small-bandgap fullerenes and other insoluble fullerenes and to very high molecular weight fullerenic materials generated in fullerenic soot, including giant fullerenes, fullerenic polymers, carbon nanotubes and metal-carbon nanoencapsulates. More specifically the invention relates to improved methods for cyclopropanation of fullerenes. Specific reaction conditions are provided which allow for cyclopropanation reactions to be successfully performed for the first time on insoluble classes of fullerenes. Also provided is a method for purification of one or more fullerenes from a fullerenic material containing the one or more fullerenes in addition to non-fullerenic carbonaceous material, particularly amorphous carbonaceous material, by derivatizing one or more fullerenes using the methods of the invention and separating soluble derivatizes fullerenes from insoluble materials.

35 Claims, 9 Drawing Sheets

U.S. PATENT DOCUMENTS

| | | | | |
|---|---|---|---|---|
| 5,648,523 | A | 7/1997 | Chiang | 562/100 |
| 5,688,486 | A | 11/1997 | Watson et al. | 424/1.65 |
| 5,717,076 | A | 2/1998 | Yamamoto et al. | 534/558 |
| 5,739,376 | A | 4/1998 | Bingel | 560/51 |
| 5,763,719 | A | 6/1998 | Gugel et al. | 585/471 |
| 5,811,460 | A | 9/1998 | Friedman et al. | 514/563 |
| 5,869,626 | A | 2/1999 | Yamamoto et al. | 534/10 |
| 5,994,410 | A | 11/1999 | Chiang et al. | 514/709 |
| 6,020,523 | A | 2/2000 | Chiang | 562/493 |
| 6,046,361 | A | 4/2000 | Chiang | 564/458 |
| 6,162,926 | A | 12/2000 | Murphy et al. | 548/417 |
| 6,204,391 | B1 | 3/2001 | Friedman et al. | 548/338.1 |
| 6,265,443 | B1 | 7/2001 | Choi et al. | 514/569 |
| 6,399,785 | B1 | 6/2002 | Murphy et al. | 548/417 |

FOREIGN PATENT DOCUMENTS

| | | |
|---|---|---|
| EP | 00782560 A1 | 7/1997 |
| EP | 00695287 B1 | 10/1997 |
| EP | 1071149 A2 | 1/2001 |
| WO | WO94/05671 | 8/1993 |
| WO | WO96/09275 | 9/1994 |
| WO | WO96/26186 | 8/1996 |
| WO | WO96/36631 | 11/1996 |
| WO | WO03/029136 | 4/2003 |

OTHER PUBLICATIONS

Solomons, Organic Chemistry, 1980, $2^{nd}$ ed. p. 615.*

Alfa Aesa, Research chemicals, metals, and materials, 1999-2000, p. 314-315.*

Akasaka, T. et al. (1995)(a). "Exohedral Adducts of La@$C_{82}$," *Nature* 374:600-601.

Akasaka, T. et al. (1995)(b). "Synthesis of the First Adducts of the Dimetallofullerenes $La_2$@$C_{80}$ and $Sc_2$@$C_{84}$ by Addition of a Disilirane," *Angew. Chem. Intl. Ed. Engl.* 34:2139-2141.

Akasaka, T. et al. (1995)(c). "Exohedral Derivatization of an Endohedral Metallofullerene Gd@$C_{82}$," *Chem. Comm.*, pp. 1343-1344.

Balch, A. L.; Olmstead, M. M. (1998). "Reactions of Transition Metal Complexes with Fullerenes ($C_{60}$, $C_{70}$, etc.) and Related Materials" *Chem. Rev.* 98:2123-2166.

Beer, F. et al. (1997). "High-Yield Reactive Extraction of Giant Fullerenes from Soot," *J. Mater. Chem.*, 7:1327-1330.

Bellavia-Lund, C. et al. (1997), "Synthesis of [70] Azafulleroids: Investigations of Azide Addition to $C_{70}$," *J. Am. Chem. Soc.* 119:943-946.

Bethune, D. S. et al. (1993) "Atoms in carbon cages: the structure and properties of endohedral fullerenes," *Nature* 366:123-128.

Beulen, M. W. J. et al. (May 2000). "Adduct Removal from Methanofullerenes via Reductive Electrochemistry," *Chem. Comm.*, pp. 917-918.

Bingel, C. (1993). "Cyclopropanierung von Fullerenen," *Chem. Ber.*, 126:1957-1959.

Bingel, C.; Schiffer, H. (1995). "Biscyclopropanation of $C_{70}$," *Liebigs Ann.*, pp. 1551-1553.

Bolskar, R.D. et al., (Apr. 2003), "First Soluble M@$C_{60}$Derivatives Provide Enhanced Access to Metallofullerenes and Permit in Vivo Evaluation of Gd@$C_{60}$[C(COOH)$_2$]$_{10}$ as a MRI Contrast Agent," J. Am. Chem. Soc. 125:5471-5478.

Braun, T.; Rausch, H. (1998). "Radioactive endohedral metallofullerenes formed by prompt gamma-generated nuclear recoil implosion," *Chem. Phys. Lett.* 288:179-182.

Brettreich, M.; Hirsch, A. (1998). "A Highly Water-Soluble Dendro[60]fullerene," *Tet. Lett.* 39:2731-2734.

Cagle, W.D. et al. (1996). "Synthesis, Characterization, and Neutron Activation of Holmium Fullerenes," *J. Am. Chem.Soc.* 118:8043-8047.

Cagle, D. W.et al. (1999) "In vivo studies of fullerene-based materials using endohedral metallofullerene radiotracers," *Proc. Natl. Acad. Sci. USA* 96:5182-5187.

Camps, X.; Hirsch, A. (1997). "Efficient Cyclopropanation of $C_{60}$ Starting from Malonates," *J. Chem. Soc. Perkin Trans.* 1, pp. 1595-1596.

Caravan, P. et al. (1999). "Gadolinium(III) Chelates as MRI Contrast Agents: Structure, Dynamics, and Applications," *Chem. Rev.* 99:2293-2352.

Cerar, J. et al. (1998), "Water-Soluble Fullerenes. 1. Fullerenehexamalonic Acid $T_h$-$C_{66}$(COOH)$_{12}$, an Intermediate Spherical Electrolyte," *J. Phys. Chem. B* 102(38):7377-7381.

Cheng, F.et al. (May 2000). "Synthesis and Optical Properties of Tetraethyl Methano[60]fullerenediphosphonate," *Tet. Lett.* 41:3947-3950.

Cross, R. J.et al. (1996). "Differentiation of Isomers Resulting from Bisaddition to $C_{60}$ Using $^3$He NMR Spectroscopy," *J. Am. Chem. Soc.* 118:11454-11459.

Diederich, F. et al. (1991) "The Higher Fullerenes: Isolation and Characterization of $C_{76}$, $C_{84}$, $C_{90}$, $C_{94}$, and $C_{70}$O, an Oxide of $D_{5h}$-$C_{70}$," *Science* 252:548-551.

Diederich, F.; Kessinger, R. (1999). "Templated Regioselective and Stereoselective Synthesis in Fullerene Chemistry," *Acc. Chem. Res.* 32:537-545.

Diener, M. D.; Alford, J. M. (1998) "Isolation and Properties of Small-Bandgap Fullerenes," *Nature* 393:668-671.

Dietel, E. et al. (1999). "Atomic Nitrogen Encapsulated in Fullerenes: Effects of Cage Variations," *J. Am. Chem. Soc.* 121:2432-2437.

Dugan, L. L. et al. (Jul. 2000). "Carboxyfullerenes as Neuroprotective Antioxidants," in *Fullerenes: Chemistry, Physics, and Technology*, Kadish, K. M. and Ruoff, R. S. eds., John Wiley & Sons, New York, pp. 467-469.

Friedman, S.H. et al. (1993), "Inhibition of the HIV-1 Protease by Fullerene Derivatives: Model Building Studies and Experimental Verification,". *J. Am. Chem. Soc.* 115:6506-6509.

Grösser, T. et al. (1995), "Ring Expansion of the Fullerene Core by Highly Regioselective Formation of Diazafulleroids," *Angew. Chem. Int. Ed. Engl.* 34(12):1343-1345.

Hawkins, J.M. (1992), "Osmylation of $C_{60}$: Proof and Characterization of the Soccer-Ball Framework," *Acc. Chem. Res.* 25:150-156.

Hinokuma, K.; Ata, M. (Jun. 2001)(a). "Fullerene Proton Conductors," *Chem. Phys. Lett.* 341:442-446.

Hirsch, A. (1999), "Principles of Fullerene Reactivity," in *Topics in Current Chemistry: Fullerenes and Related Structures*, Springer-Verlag, New York, 199:2-65.

Hirsch, A. et al. (1994), "Regiochemistry of Multiple Additions to the Fullerene Core: Synthesis of a T$h$-Symmetric Hexakisadduct of $C_{60}$ with Bis(ethoxycarbonyl)methylene," *J. Am. Chem. Soc.* 116:9385-9386.

Hirsch, A. et al. (1992), "Titration of $C_{60}$: A Method for the Synthesis of Organofullerenes," *Angew. Chem. Int. Ed. Engl.* 31(6):766-768.

Hirsch, A. (1994)(a). *The Chemistry of the Fullerenes*, Georg Thieme Verlag Stuttgart, New York.

Hirsch, A.; Lamparth, I.; Karfunkel, H. R. (1994)(b). "Fullerene Chemistry in Three Dimensions: Isolation of Seven Regioisomeric Bisadducts and Chiral Trisadducts of $C_{60}$ and Di(ethoxycarbonyl)methylene," Angew. Chem. Int. Ed. 33:437-438.

Illescas, B. et al. (1997), "[60]Fullerene-Based Electron Acceptors with Tetracyano-p-quinodimethane (TCNQ) and Dicyano-p-quinonediimine (DCNQI) Derivatives," *Tetrahedron Lett.* 38(11):2015-2018.

Inoue, T. et al. (Jan. 2000). "Electronic Structure of Eu@$C_{60}$ Studied by XANES and UV-VIS Absorption Spectra," *Chem. Phys. Lett.* 316:381-386.

Jung, M. E. (1991). "Stabilized Nucleophiles with Electron Deficient Alkenes and Alkynes," in *Comprehensive Organic Synthesis: Selectivity, Strategy, & Efficiency in Modern Organic Chemistry*, Trost, B. M.; Fleming, I. eds., Pergamon Press, Oxford, vol. 4, pp. 1-67.

Kato, T. et al. (1997). "Chemical Reactivities of Endohedral Metallofullerenes," *J. Phys. Chem. Solids* 58:1779-1783.

Kessinger, R. et al. (1998). "Walk On the Sphere: Electrochemically Induced Isomerization of $C_{60}$ Bis-adducts by Migration of Di(alkoxycarbonyl)methano Bridges," *J. Am. Chem. Soc.* 120:8545-8546.

Khong, A. et al. (Apr. 2000). "From $^3$He@$C_{60}$ to $^3$H@$C_{60}$: Hot-Atom Incorporation of Tritium in $C_{60}$," *J. Am. Chem. Soc.* 104:3940-3943.

Kitagawa, T. et al. (1999), "Electrophilic Addition of Polychloroalkanes to $C_{60}$: Direct Observation of Alkylfullerenyl Cation Intermediates," J. Am. Chem. Soc. 121:4298-4299.

Klos, H. et al. (1994). "Doping of $C_{60}$ with Tertiary Amines: TDAE, DBU, DBN. A Comparative Study," Chem. Phys. Lett. 224:333-337.

Krätschmer, W. et al. (1990) "Solid $C_{60}$: A New Form of Carbon," Nature 347:354-358.

Krusic, P.J. et al. (1991), "Radical Reactions of $C_{60}$," Science 254:1183-1185.

Kubozono, Y. et al. (1995). "Preparation and Extraction of Ca@$C_{60}$," Chem. Lett. pp. 457-458.

Kubozono, Y. et al. (1996)(a). "Extractions of Ca@$C_{60}$ and Sr@$C_{60}$ with Aniline," Chem. Lett. pp. 453-454.

Kubozono, Y. et al. (1996)(b). "Extractions of Y@$C_{60}$, Ba@$C_{60}$, La@$C_{60}$, Ce@$C_{60}$, Pr@$C_{60}$, Nd@$C_{60}$, and Gd@$C_{60}$ with Aniline," J. Am. Chem. Soc. 118:6998-6999.

Lamparth, I.; Hirsch, A. (1994). "Water-Soluble Malonic Acid Derivatives of $C_{60}$ with a Defined Three-Dimensional Structure," Chem. Comm., pp. 1727-1728.

Lamparth, I. et al. (1997). "Side-Chain Modification of $C_{60}$ via Activation of the Easily Accesible Fulleromalonic Acid $C_{61}(COOH)_2$," Liebigs Ann./Recueil, pp. 253-258.

Liu et al. (1998) "High Efficient Extraction of M@$C_{2n}$ (M = La, Ce) by a High Pressure and High Temperature Method," Tetrahedron 54:11123-11128.

Liu, S.; Sun, S. (Apr. 2000) "Recent progress in the studies of endohedral metallofullerenes," J. Organomet. Chem. 599:74-86.

Maggini, M. et al. (1994), "Addition Reactions of $C_{60}$ Leading to Fulleroprolines," J. Chem. Soc., Chem. Commun, pp. 305-306.

McHenry, M. E.; Subramoney, S. (Jul. 2000). "Synthesis, Structure, and Properties of Carbon Encapsulated Metal Nanoparticles," in Fullerenes: Chemistry, Physics, and Technology, Kadish, K. M. and Ruoff, R. S. eds., John Wiley & Sons, New York, pp. 839-885.

Mikawa, M. et al. (Jun. 2001). "Paramagnetic Water-Soluble Metallofullerenes Having the Highest Relaxivity for MRI Contrast Agents," Bioconj. Chem., 12:510-514.

Moonen, N. N. P. et al. (Mar. 2000). "The Chemical Retro-Bingel Reaction: Selective Removal of Bis(alkoxycarbonyl)methano addends from $C_{60}$ and $C_{70}$ with Amalgamated Magnesium," Chem. Comm., pp. 335-336.

Nagase, S. et al. (1996) "Endohedral Metallofullerenes: New Spherical Cage Molecules with Interesting Properties," Bull. Chem. Soc. Jpn. 69:2131-2142.

Nagase, S. et al. (Jul. 2000) "Endohedral Metallofullerenes: Theory, Electrochemistry, and Chemical Reactions," in Fullerenes: Chemistry, Physics, and Technology, Kadish, K. M. and Ruoff, R. S. eds., John Wiley & Sons, New York, pp. 395-436.

Nierengarten, J.-F.; Nicoud, J.-F. (1997). "Cyclopropanation of $C_{60}$ with Malonic Acid Mono-Esters," Tet. Lett., 38:7737-7740.

Nierengarten, J.-F. et al. (1997), "Macrocyclization on the Fullerene Core: Direct Regio- and Diastereoselective Multi-Functionalization of [60]Fullerene, and Synthesis of Fullerene-dendrimer Derivatives," Helv. Chim. Acta. 80:2238-2276.

Nierengarten, J.F. et al. (1997), "Methanofullerene Molecular Scaffolding: Towards $C_{60}$-Substituted Poly(triacetylenes) and Expanded Radialenes, Preparation of a $C_{60}$-$C_{70}$ Hybrid Derivative, and a Novel Macrocyclization Reaction," Helv. Chim. Acta 80:293-316.

Nuretdinov, I. A. et al. (Dec. 2000). "Synthesis of Phosphorylated Methanofullerenes," Russ. Chem. Bull. 49:2048-2050.

Okada, S.; Saito, S. (Apr. 2000), "Stable Polymers of $C_{74}$ and $C_{78}$ Fullerenes," Chem. Phys. Lett. 321:156-162.

Ogawa, T. et al. (Mar. 2000), "Isolation and Characterization of Er@$C_{60}$," J. Am. Chem. Soc. 122:3538-3539.

Parker, D. H. et al. (1991). "High-Yield Synthesis, Separation, and Mass-Spectrometric Characterization of Fullerenes $C_{60}$ to $C_{266}$," J. Am. Chem. Soc. 113:7499-7503.

Pellicciari, R. et al. (Dec. 2000). "Synthesis of Methano[60]fullerenephosphonic- and Methano[60]fullerenediphosphonic Acids," Synlett, pp. 1816-1818.

Prato, M. et al. (1998), "Fulleropyrrolidines: A Family of Full-Fledged Fullerene Derivatives," Acc. Chem. Res. 31(9):519-526.

Rapenne, G. et al. (1999). "Regioselective one-step synthesis of trans-3,trans-3,trans-3 and e,e,e [60]fullerene tris-adducts by a $C_3$-symmetrical cyclotriveratrylene tether," J. Chem. Soc. Chem. Commun. pp. 1121-1122.

Reed, C. A.; Bolskar, R. D. (Feb. 2000) "Discrete Fulleride Anions and Fullerenium Cations," Chem. Rev. 100:1075-1120.

Reuther, U. et al. (May 2002). "A Highly Regioselective Approach to Multiple Adducts of $C_{60}$ Governed by Strain Minimization of Macrocyclic Malonate Addends," Chem. Eur. J. 8:2261-2273.

Richardson, C. F. et al. (Mar. 2000). "Synthesis and Characterization of Water-Soluble Amino Fullerene Derivatives," Org. Lett. 2:1011-1014.

Ruoff, R. S. et al. (1993) "Solubility of $C_{60}$ in a Variety of Solvents," J. Phys. Chem. 97:3379-3383.

Satoh, M. et al. (1997), "Inhibitory Effects of a Fullerene Derivative, Dimalonic Acid C60, on Nitric Oxide-Induced Relaxation of Rabbit Aorta," Eur. J. Pharmacol. 327:175-181.

Schinazi, R.F. et al. (1993), "Synthesis and Virucidal Activity of a Water-Soluble, Configurationally Stable, Derivatized $C_{60}$ Fullerene," Antimicrob. Agents Chemother. 37(8):1707-1710.

Shinohara, H. (Jul. 2000). "Endohedral Metallofullerenes: Production, Separation, and Structural Properties," in Fullerenes: Chemistry, Physics, and Technology, Kadish, K. M. and Ruoff, R. S. eds., John Wiley & Sons, New York, pp. 357-393.

Shinohara, H. (Jun. 2000). "Endohedral Metallofullerenes," Rep. Prog. Phys. 63:843-892.

Skiebe, A. et al. (1994). "[DBU]$C_{60}$. Spin Pairing in a Fullerene Salt," Chem. Phys. Lett. 220:138-140.

Stevenson, S. et al. (1999) "Small-bandgap endohedral metallofullerenes in high yield and purity," Nature 401:55-57.

Sun, D. et al. (1999) "A Simple Method for the Selective Enrichment of Endohedral Metallofullerenes," Chem. Mater. 11:374-377.

Sun, Y.-P. et al. (1997), "Photochemical Preparation of Highly Water-Soluble Pendant (60) Fullerene-Aminopolymers," Photochem. Photobiol. 66(3):301-308.

Sun, Y.-P. et al. (1996), "Preparation and Characterization of a Highly Water-Soluble Pendant Fullerene Polymer," Chem. Commun., pp. 2699-2700.

Suzuki, T. et al. (1995). "Chemical Reactivity of a Metallofullerene: EPR Study of Diphenylmethano-La@$C_{82}$ Radicals," J. Am. Chem. Soc. 117:9606-9607.

Tagmatarchis, N. et al. (Jul. 2001). "Novel Singlet Oxygen Generators: The Nature and the Number of Trapped Metal Atoms in Endohedral Metallofullerenes M@$C_{82}$ (M = Dy, Gd, La) and $Dy_2$@$C_{2n}$ (2n=84-94)," Phys. Chem. Chem. Phys. 3:3200-3202.

Taylor, R. et al. (1998). "$C_{60}$ Degrades to $C_{120}O$," Chem. Comm., pp. 2497-2498.

Thrash, T.P. et al. (1999). "Toward Fullerene-based Radiopharmaceuticals: High-Yield Neutron Activation of Endohedral [165]Ho Metallofullerenes," Chem. Phys. Lett. 308:329-336.

Tokuyama, H. et al. (1993), "Photoinduced Biochemical Activity of Fullerene Carboxylic Acid," J. Am. Chem. Soc. 115:7918-7919.

Tomberli, V. et al. (Nov. 2000), "Synthetic Approaches towards the Preparation of Water-Soluble Fulleropyrollidines," Carbon 38:1551-1555.

Tsai, M.-C. (1997), "Polyhydroxylated C60, Fullerenol, a Novel Free-radical Trapper, Prevented Hydrogen Peroxide- and Cumene Hydroperoxide-elicited Changes in Rat Hippocampus In-Vitro," J. Pharm. Pharmacol. 49:438-445.

Ulmer, L. et al. (1998), "Mono-and Bisfunctionalization of Fullerenes with N-Containing Reactants," J. Inf. Rec. 24(3-4):243-247.

Wei, X.-W. et al. (Aug. 2001), "The Remarkable Stable Emerald Green $C_{60}F_{15}[CBr(CO_2Et)_2]_3$: The First [60] Fullerene That Is Also the First [18]Trannulene," Angew. Chem. Intl. Ed. 40:2989-2992.

Wharton, T. et al. (Jul. 2001), "New Non-Ionic, Highly Water-Soluble Derivatives of $C_{60}$ Designed for Biological Compatibility," Tet. Lett. 42:5159-5162.

Wilson, L. J. (1999). "Medical Applications of Fullerenes and Metallofullerenes," Electrochemical Society Interface, Winter Issue, 24-28.

Wilson, S. R. (Jul. 2000)(a). "Biological Aspects of Fullerenes," in *Fullerenes: Chemistry, Physics, andTechnology*, Kadish, K. M. and Ruoff, R. S. eds., John Wiley & Sons, New York, 437-465.

Wilson, S. R. et al. (Jul. 2000)(b). "Organic Chemistry of Fullerenes," in *Fullerenes: Chemistry, Physics, andTechnology*, Kadish, K. M. and Ruoff, R. S. eds., John Wiley & Sons, New York, 91-176.

Wolff, D.J. et al. (Mar. 2002), "Trisamine $C_{60}$-Fullerene Adducts Inhibit Neuronal Nitric Oxide Synthase by Acting as Highly Potent Calmodulin Antagonists," *Arch. Biochem. Biophys.* 339(2):130-141.

Wolff, D.J. et al. (2001, first published Dec. 2000), "$C_{60}$-Fullerene Monomalonate Adducts Selectively Inactivate Neuronal Nitric Oxide Synthase by Uncoupling the Formation of Reactive Oxygen Intermediates from Nitric Oxide Production," *Biochemistry* 40(1):37-45.

Wolff, D.J. et al. (Jun. 2000), "Inhibition of Nitric Oxide Synthase Isoforms by Tris-Malonyl-$C_{60}$-Fullerene Adducts," *Arch. Biochem. Biophys.* 378(2):216-223.

Wudl, F. (1992), "The Chemical Properties of Buckminsterfullerene ($C_{60}$) and the Birth and Infancy of Fulleroids," *Acc. Chem. Res.* 25(3):157-161.

Yeretzian, C.; Wiley, J. B.; Holczer, K.; Su, T.; Nguyen, S.; Kaner, R. B.; Whetten, R. L. (1993) "Partial Separation of Fullerenes by Gradient Sublimation," *J. Phys. Chem.* 97:10097-10101.

Zhang, S.; Sun, D.; Li, X.; Pei, F.; Liu, S. (1997). "Synthesis and Solvent Enhanced Relaxation Property of Water-Soluble Endohedral Metallofullerenes," *Fullerene Sci. Tech.* 5:1635-1643.

\* cited by examiner

DERIVATIZATION AND SOLUBILIZATION OF INSOLUBLE CLASSES OF FULLERENES

CROSS-REFERENCE TO RELATED APPLICATIONS

This application claims priority to U.S. provisional application Ser. No. 60/326,353 filed Oct. 1, 2001 and to U.S. provisional application Ser. No. 60/371,380 filed Apr. 9, 2002, which are both incorporated by reference herein in their entirety.

ACKNOWLEDGEMENT OF GOVERNMENT SUPPORT

This invention was made under a grant from the United States government through the National Institutes of Health Grant No. 5R44CA066363-03. The United States government has certain rights in this invention.

BACKGROUND OF THE INVENTION

This invention describes improved methods for derivatization and solubilization of fullerenes.

Since fullerenes were first macroscopically produced by the arc method in 1990 (Krätschmer, 1990), their exohedral derivatization chemistry has proceeded. The organic functionalization of fullerenes has been extensively reviewed (Hirsch, 1994(a); Wilson, 2000(a, b)) as well as their inorganic/organometallic functionalization chemistry (Balch, 1998). Because fullerenes possess no substituents, their exohedral derivatization chemistry begins exclusively with addition reactions to their carbon surface, most commonly by 1,2 bis-addition across the reactive carbon-carbon double bonds of the fullerene.

A fundamental characteristic of fullerenes is their electrophilic nature (Reed, 2000) and as a consequence most reported derivatization involves the addition of nucleophilic reagents. A particular kind of nucleophilic addition of widely recognized utility is cyclopropanation which was first reported by Bingel (Bingel, 1993). A general example of this so-called "Bingel" reaction is illustrated by the series of steps shown below in FIG. 1.

Many scientific papers and reports concern the Bingel-type cyclopropanation of the fullerene surface (Bingel, 1993; Bingel, 1995; Bingel, 1998 as well as PCT-WO96/09275A1, EP00695287B1, and EP00782560A1; Brettreich, 1998; Camps; 1997; Hirsch, 1994(a); Hirsch, 1994(b); Lamparth, 1994; Lamparth, 1997; Nierengarten, 1997; Richardson, 2000; Wei, 2001; Wharton, 2001; Wilson 2000(b)). A primary reference for general organic reactions between stabilized nucleophiles and electron-deficient alkenes (non-fullerenes) is that of Jung (1991).

The earliest examples of Bingel-type cyclopropanation of the fullerene surface involved base-induced deprotonation of an α-halo ketone, forming a relatively stabilized nucleophilic carbanion that attacks the electron deficient fullerene. Bingel's initial study employed NaH as the base, which forms gaseous hydrogen by combination of the metal hydride and the removed proton (Step 1). The incipient Na$^+$ salt of the carbanion may be very strongly ion paired in the nonpolar solvents typically used (toluene, etc.). The carbanion may be partially stabilized by adjacent electron withdrawing substituents (the α-halogen, carbonyls, phenyls, etc. that are electronegative and/or inductively withdraw electron density) that simultaneously may or may not additionally enhance stability via electron delocalization (resonance).

The nucleophilic carbanion immediately attacks the fullerene, forming a new bond (Step 2). The cyclopropanation is complete following the spontaneous elimination of the halide anion (or other current leaving group) (Step 3). The net reaction thus occurs via an addition/elimination mechanism. While the mechanism illustrated in FIG. 1 is believed to be the most likely mechanism for the reaction, less-likely alternatives exist including a concerted reaction and an electron transfer route. By using excess quantities of reagents, multiple groups can be added to the fullerene surface. The different products with different numbers of groups added and with different isomeric arrangements on the fullerene surface can then be purified and separated from one another by chromatography. The fullerenes derivatized by cyclopropanation can also be referred to as methanofullerenes. When the Bingel reaction is performed on fullerenes that are already derivatized, for example $C_{60}F_{18}$, the α-halo substituent of the nucleophile may not function as the leaving group. Instead, a group previously on the fullerene departs leaving the nucleophile group attached to the fullerene via the α-sp$^3$ carbon without cyclopropanation (Wei, 2001).

Conditions alternative to those used by Bingel in his first report have been developed. One of the most popular changes has been the replacement of the insoluble base NaH with soluble amines, most notably DBU (1,8-diazabicyclo[5.4.0]undec-7-ene) (Camps, 1997). While this base is strongly hindered, it has been reported to readily form covalent bonds with the surface of $C_{60}$ (Skiebe, 1994; Klos, 1994).

Another modification to the standard Bingel conditions reported is the incipient production of the reactive α-halo compounds by in situ treatment of mono- and bis-malonates with halogen-releasing agents such as $CBr_4$, $I_2$, etc. (Camps, 1997; Nierengarten, 1997). This allows for the use of more elaborately substituted malonates for which the α-halo precursor is difficult to individually prepare and/or isolate as a reagent. Bingel-style addition of malonates has been used to link fullerenes to a variety of substituents of interest, for example, porphyrins.

Addition of multiple groups to fullerene surfaces is usually performed stepwise using excess reagents. Derivatives with specific numbers of addends can be separated from derivatives with lesser or greater numbers of addends by chromatographic or other standard techniques. Separation of the different regioisomers formed can also be performed chromatograpically, but such separations can be expensive and laborious.

For a Bingel-style multi-derivatization, a tether-directed addition strategy offers control over regiospecificity of addition (location pattern of the cyclopropanations) and the number of addend groups in a pre-determined way while increasing yields over traditional derivatization strategies, as reviewed by Diederich et. al. (Diederich, F.; Kessinger, R. (1999). "Templated Regioselective and Stereoselective Synthesis in Fullerene Chemistry," Acc. Chem. Res., 32, 537-545). The tether strategy uses multi-functional reaction substrates cojoined in one molecule by covalent moieties of variable length separating these functionalities, which are themselves variable in number.

Tether-directed formation of $C_{60}$ trisadducts has been reported previously by Rapenne et. al. (Rapenne, G.; Crassous, J.; Collet, A.; Echegoyen, L.; Diederich, F. (1999). "Regioselective one-step synthesis of trans-3, trans-3, trans-3 and e, e, e [60]fullerene tris-adducts by a $C_3$-symmetrical cyclotriveratrylene tether," J. Chem. Soc. Chem. Commun. 1121-1122). Reuther et al. describe the use of cyclo-[n]-octylmalonates as an improved tether strategy (Reuther, U.; Brandmüller, T.; Donaubauer, W.; Hampel, F.; Hirsch, A.

(2002). "A Highly Regioselective Approach to Multiple Adducts of $C_{60}$ Governed by Strain Minimization of Macrocyclic Malonate Addends," *Chem. Eur. J.*, 8, 2261-2273). Reuther et. al. used this Bingel-reaction based tether addition process to form the $C_3$ isomer (or e, e, e isomer) of the trisadduct $C_{60}[C(COOH)_2]_3$ in high yield with high specificity. Bingel-style addition of malonates has also been used to control the regiochemistry of addition by Wilson (Wilson, 2000(b)).

Following the Bingel cyclopropanation, the ester groups of malonate addition products can be cleaved and converted to other functionalities, i.e. effecting side-chain modification (Lamparth, 1997). For example, the ester groups of the Bingel addition product of diethylbromomalonate (FIG. 1) can be converted to their respective carboxylic acids (or carboxylate salts of alkali metals, etc.) using the method of Hirsch (Lamparth, 1994). The carboxylic acid and carboxylate salts (of multiple adducts) of the fullerenes are water-soluble, a property critical to the development of the fullerenes' emerging medical applications. For example, multiply carboxylated $C_{60}$ has shown high potential as an antioxidant for treating neurodegenerative disorders in vivo (Dugan, 2000). Other potential pharmaceutical applications for water-solubilized fullerenes include HIV-protease inhibitors (Wilson, 2000(a)), nuclear medicine agents (Cagle, 1999), and in vivo enhancers for medical imaging techniques including, e.g., MRI, X-ray, and nuclear imaging (Zhang, 1997; Wilson, 1999; Mikawa, 2001).

Typically, the Bingel-style cyclopropanation reactions of non-derivatized fullerenes have been conducted in non-polar solvents such as aromatic hydrocarbons (benzene, toluene, etc.) that are also good solvents for common fullerenes (Ruoff, 1993). The fullerenes derivatized in this manner have invariably belonged to the class of fullerenes possessing larger HOMO-LUMO gaps such as the most abundant fullerene, $C_{60}$, and the larger "higher" $C_{2n}$ fullerenes, e.g. $C_{70}$, $C_{76}$, $C_{78}$, $C_{82}$, $C_{84}$, etc. A notable property of these large HOMO-LUMO gap-possessing fullerenes is solubility in common non-polar organic solvents. Consequently, addition reactions like the Bingel method outlined above are performed on solutions of these fullerenes. This excludes important classes of fullerene materials that are not soluble in these common organic solvents. U.S. Pat. No. 5,739,376, issued to Bingel, reports formation of cyclopropanated derivatives of fullerenes in polar solvents including methylene chloride and chlorobenzene. The fullerenes discussed in Bingel's patent ($C_{60}$, $C_{70}$, $C_{76}$, $C_{78}$) are expected to be soluble in these polar aprotic solvents prior to derivatization. PCT published application WO 96/09275 of Bingel also reports the generation of fullerene derivatives by certain cyclopropanation reactions.

Chemical and electrochemical retro-Bingel reactions have been demonstrated by Echegoyen et al. (Moonen, 2000; Beulen, 2000). Addition of excess electrons (via exhaustive reduction) to methanofullerene derivatives regenerates underivatized fullerenes. Addition of less than an excess amount of electrons induces only a substituent migration or a "walk-on-the-sphere" isomerization of the methanofullerene groups (Kessinger, 1998).

There are a number of additional reports of methods for derivatization of fullerenes. Gugel, U.S. Pat. No. 5,763,719, reports methods for making thermally stable fullerenes. Murphy et. al., U.S. Pat. No. 6,162,926 and PCT published application WO9636631, report methods for making multiply-substituted fullerenes. Cahill and Henderson, U.S. Pat. No. 5,475,172, report methods of functionalizing fullerenes employing organoborane intermediates. Mattay et. al., PCT published application WO 9626186, reports methods for the generation of azafullerenes. Hinokuma et. al., EP 1 071149, reports the introduction of one or more proton releasable groups such as OH and $SO_3H$ into fullerenes. Kampe et. al., U.S. Pat. No. 5,587,476 and PCT published application WO 9405671, report fullerene derivatives prepared by reaction with diamines. Chiang, U.S. Pat. Nos. 5,648,523; 5,994,410; 6,020,523 and 6,046,361, reports the preparation of fullerene derivatives including polyorganofullerenes and water-soluble fullerene derivatives. Friedman et. al., U.S. Pat. Nos. 5,811,460 and 6,204,391, report water-soluble fullerene derivatives. Schriver et. al., U.S. Pat. No. 5,503,643, reports fuel oil-substituted fullerenes.

Endohedral fullerenes are those fullerenes encapsulating an atom or atoms in their hollow interior spaces. They are written with the general formula $M_m@C_{2n}$, where M is an element, m is the integer 1, 2, 3 or higher, and n is an integer number. The "@" symbol refers to the endohedral or interior nature of the M atom inside of the fullerene cage. Aspects of endohedral metallofullerenes have been reviewed (Bethune, 1993; Nagase, 1996; Nagase, 2000; Shinohara, 2000; Liu, 2000).

Endohedral fullerenes corresponding to most of the empty fullerene cages have been produced and detected under varied conditions. Because the endohedral element is completely encased by the spherical fullerene shell, it is not released to the exterior except under cage-destructive conditions (heat, long-duration exposure to strong acids, etc.). Endohedrals containing lanthanide, transition, alkali, and alkaline earth metals have by far received the most attention to date, although studies on non-metallo endohedrals such as $He@C_{60}$, $N@C_{60}$, $P@C_{60}$, etc. are developing. The major production technique for producing endohedral metallofullerenes is the Krätschmer-Huffman style resistive heating of graphite rods that are impregnated with metals or metal salts. Typically, metallofullerenes comprise only several percent of the total fullerene yield in the carbon arc production method.

Of the $M_m@C_{2n}$ metallo-endohedrals, those having the particular formulation $M@C_{82}$ (with M=a lanthanide element) have been the subjects of most investigations to date. This is largely due to the solubility of the $M@C_{82}$ closed-shell species in common solvents. Because of their solubility, they can be separated from the empty fullerenes and other endohedral metallofullerenes, including their different cage isomers, by chromatographic methods. Their solubility also allows for standard derivatizations to be performed on the metallo-endohedral fullerenes, by analogy to the derivation of empty large HOMO-LUMO gap fullerenes.

The study of other $M@C_{2n}$, and multiple-metal containing $M_m@C_{2n}$ materials is proceeding at more slowly because many of these fullerenes are intrinsically insoluble in the common, non-reactive hydrocarbon and arene solvents normally used for $C_{60}$, etc. Without wishing to be bound by any particular theory, the most likely explanation for their insolubility is the spontaneous formation of intramolecular polymers.

The "polymerization" which occurs for certain metallofullerenes, most notably the $M@C_{60}$ species, derives from their electronic structures. The electronic structure of a metallofullerene of course encompasses the interior metal and any electrons it donates to the fullerene cage molecular orbital. Essentially, these fullerenes have small HOMO-LUMO or band gaps such that the molecules are open-shell or very close in energy to being open shell. Functionally equivalent descriptions to this situation include the descriptions that metallofullerenes possess "radical sites", "dangling bonds", or "unfulfilled vacancies". Most endohedral metallofullerenes have been found to contain metals which donate three electrons (per metal) forming endohedral $M^{3+}$ ions inside of a fullerene cage now having three "extra" electrons relative to a cage without a metal inside. Such an endohedral metallofullerene molecule is a zwitterion, with a cationic metal "core" and anionic fullerene (fulleride) cage.

Because the number of electrons transferred to the fullerene cage (three) is an odd number, there has to be an unpaired electron, i.e. the molecule is a radical. As many radicals do, they dimerize or oligomerize spontaneously "quenching" their free radical status. To free them from their intramolecularly cross-linked matrix, their electronic structures must be altered. To eliminate radical behavior, redox chemistry (addition or removal of molecular electron(s)) can be performed, or they can be derivatized exohedrally by substituent groups. It should be pointed out that the matrix of "polymerized" insoluble endohedral fullerenes likely contains some small percentage of soluble $C_{2n}$ species interstitially trapped and/or bonded to other endohedral fullerenes, as a consequence of heterogeneous nature of fullerene generation in the arc process.

Despite the relatively low availability of samples of endohedral fullerenes, their derivatization chemistry is also proceeding (Kato, 1997). Examples include the derivatization of the soluble endohedral metallofullerenes $M@C_{82}$ (M=La, Gd), $La_2@C_{80}$, and $Sc_2@C_{84}$ with disiliranes and digermanes (Akasaka, 1995(a); Akasaka, 1995(b); Akasaka, 1995(c); Yamamoto, 1999). Suzuki and co-workers reported the reaction of $La@C_{82}$ with substituted carbenes derived from diazomethanes to produce cyclopropanated derivatives (Suzuki, 1995; Yamamoto, 1998). Various groups have reported the polyhydroxylation of endohedral metallofullerenes including $Ho@C_{82}$ (Cagle, 1999), $Ho_2@C_{82}$ (Cagle, 1999), $Pr@C_{82}$ (Sun, 1999), and $Gd@C_{82}$ (Wilson, 1999; Mikawa, 2001).

Patents involving the exohedral derivatization of endohedral metallofullerenes include U.S. Pat. No. 5,717,076 (Yamamoto, 1998) and U.S. Pat. No. 5,869,626 (Yamamoto, 1999). The first involves cyclopropanations conducted in a completely different manner than Bingel-style reactions and adding four or fewer groups to the fullerene surface, while the second is an unrelated type of derivatization.

Bingel-style cyclopropanations have not been reported on endohedral metallofullerenes. Bingel-style cyclopropanations have been reported on minute amounts of "inert" endohedral fullerenes present in trace levels ($10^{-4}$ M or 100 ppm) in $C_{60}$ matrices, including $N@C_{60}$ (Dietel, 1999), $^3He@C_{60}$ (Cross, 1996) (and $^3H@C_{60}$ (Khong, 2000)). These materials were produced for EPR and $^3$He-NMR detection purposes. Both techniques are very sensitive to trace amounts of spectroscopically active material present in a matrix of dominantly unactive material. Neither has radical character expressed by the fullerene cage, explaining their apparent solubility and lack of difference in reactivity for Bigel-style cyclopropanation from that of $C_{60}$.

Reaction of $M@C_{60}$ (and $M@C_{70}$, etc.) with nucleophilic solvents to extract soluble surface-modified (normally insoluble) $M@C_{2n}$ species has been demonstrated with the nitrogen-bases aniline and pyridine. Examples of solvents used and endohedral fullerenes extracted include: aniline for $M@C_{60}$ (M=Y, Ba, La, Ce, Pr, Nd, Gd; Kubozono, 1996(b)), aniline for $Eu@C_{60}$ (Inoue, 2000), aniline for $Er@C_{60}$ (Ogawa, 2000), aniline for $Ca@C_{60}$ and $Sr@C_{60}$ (Kubozono, 1996(a)), pyridine for $Ca@C_{60}$ (Kubozono, 1995), and pyridine for mixed $M@C_{2n}$ (M=La, Ce; Liu 1998). These highly nucleophilic solvents, with strongly coordinating amine nitrogen groups, may irreversibly produce soluble, poly-solvent coordinated species. The chemical nature of the surface attachment has not been analytically determined; a covalent linkage is most likely. The formation of adducts may proceed via charge-transfer, donor-acceptor complexes, and/or reduced fullerene species prior to covalent bond formation (Skiebe, 1994; Klos, 1994). In general, the solvent molecules in these cases cannot be removed from bonding to the fullerene cages, for example by applying reduced pressure and/or non-destructive heat.

Gügel, Müllen and co-workers reported the extraction of giant fullerenes from arc-produced fullerene soot by an irreversible Diels-Alder cycloaddition strategy using ortho-quinodimethanes (Beer et. al.,1997). These highly reactive intermediates, obtained by thermal extrusion of sulfur dioxide from the requisite organic thiophenes, add irreversibly across fullerene carbon-carbon double bonds. Other reports on giant fullerene and SBF solubilizations include the following. There are several reports of solvent extraction of "giant" fullerenes $C_{2n}$ ($n \geq 50$) with high-boiling arene solvents (Parker, 1991; Diederich, 1991). Yeretzian et. al. conducted a study of gradient sublimation on empty and endohedral metallofullerenes, showing that the technique could be used to generate a partial enrichment of the larger (empty) $C_{2n}$ ($n \geq 47$) fullerenes without solvents (Yeretzian, 1993). The SBF $C_{74}$ specifically was solubilized by electrochemical one-electron reduction, which was used to separate it from the more numerous large-bandgap fullerenes (Diener, 1998).

The medicinal applications of fullerene compounds have been reviewed by several authors (Wilson, 1999; Wilson, 2000(a)). Watson et. al. mention use of endohedral fullerenes in applications like medical imaging in their U.S. patent (Watson, 1997), but provide few details on how the application would be achieved. Gd chelates as MRI contrast agents have been thoroughly reviewed by Caravan and others (Caravan, 1999). Zhang (1997), Wilson (1999), and Mikawa (2001) reported aqueous relaxivity measurements on $Gd@C_{82}(OH)_x$, showing higher $R_1$ values than obtained with conventional inorganic chelates. Neutron activation of $^{165}Ho_m@C_{2n}$ to $^{166}Ho_m@C_{2n}$ with a biodistribution study was reported (Cagle, 1996; Cagle, 1999). Dugan and co-workers have reported medicinal antioxidant and other properties of "Bingelated" $C_{60}$ (Dugan, 2000).

There remains a need in the art for improved methods of derivatization and/or solubilization of fullerenes, especially of non-derivatized and derivatized fullerenic species that are insoluble or substantially insoluble in polar aprotic solvents.

SUMMARY OF THE INVENTION

This invention describes improved methods for the derivatization and solubilization of fullerenes, which are particularly useful for those fullerenes that are normally insoluble and which are specifically applied, among others, to endohedral fullerenes, including endohedral metallofullerenes; empty fullerenes, including small-bandgap fullerenes and other insoluble fullerenes and to very high molecular weight fullerenic materials generated in fullerenic soot, including giant fullerenes, fullerenic polymers, carbon nanotubes and metal-carbon nanoencapsulates. The improved methods can also be generally applied to soluble fullerenes to improve the speed or efficiency of derivatization. The improved methods herein can further be applied to fullerenes that already contain one or more functional groups on their surfaces, i.e., derivatized fullerenes, and particularly to derivatized fullerenes that are not soluble or are only partially soluble in a selected solvent, to increase the number of functional groups on the already derivatized fullerene and/or increase the solubility of the further derivatized fullerene in a selected solvent.

The methods herein can be applied to form derivatives containing one or more exohedral functional groups on fullerene species. More specifically the invention relates to improved methods for cyclopropanation of fullerenic species which are particularly useful for derivatization of the exterior surface of insoluble fullerenic species, including insoluble empty fullerenes, endohedral fullerenes and very high molecular weight fullerenic species (i.e., giant fullerenes, carbon nanotubes and metal-carbon nanoencapsulates). As used herein cyclopropanation refers to the formation of a cyclopropyl ring by C addition to the fullerene surface and to silacyclopropanation which forms a silacyclopropyl ring by Si addition to the fullerene surface. An important aspect of this invention is the provision of specific reaction conditions which allow for cyclopropanation reactions to be successfully performed for the first time on insoluble classes of fullerenes.

In specific embodiments, the derivatives formed have increased solubility in solvents commonly employed for fullerenes (e.g., non-polar hydrocarbon and arene solvents) facilitating separation and purification of fullerenic species and/or enhancing the scope of applications of the fullerene species. In other specific embodiments, the derivatives formed have increased solubility in water facilitating separation and purification and/or enhancing the scope of applications of the fullerenic species. Thus, the invention provides methods for derivatization of fullerenic species as well as methods for solubilization of insoluble fullerenic species in a selected solvent or type of solvent through derivatization with exohedral functional groups which enhance solubility in that solvent or solvent type. The invention further provides methods for purification of normally insoluble fullerenic species from normally soluble fullerenic materials and more importantly from other normally insoluble fullerenic species. For example, derivatization and solubilization of normally insoluble fullerenic species facilitates the application of separation and purification methods that are known in the art and have been applied to the separation and purification of normally soluble fullerenic species, such as chromatographic separations and recrystallization methods.

Derivatives of fullerenic species may remain insoluble or have low solubility in common solvents. Therefore the method of this invention can also be applied to fullerenic species that carry one or more functional groups (i.e., derivatized fullerenic species) made by any known method and particularly to those derivatized fullerenic species which remain insoluble or substantially insoluble in common solvents. In particular the method is useful for further derivatization of derivatized fullerenic species which are insoluble, substantially insoluble or slightly soluble in non-polar aprotic organic solvents and polar aprotic organic solvents.

The invention also provides derivatized fullerenic species, particularly derivatives of normally insoluble fullerenes, particularly those of endohedral fullerenes, empty small-band gap and other insoluble empty fullerenes, and very high molecular weight fullerenic species. The derivatized fullerenic species of the invention may carry one or more functional groups.

The invention further provides a method for purification of one or more fullerenes from a fullerenic material containing the one or more fullerenes in addition to non-fullerenic carbonaceous material, particularly amorphous carbonaceous material. The method is particularly useful for application to one or more fullerenes that are insoluble in typical non-polar solvents. In this method the one or more fullerenes are derivatized with a cyclopropanation reagent to at least add a sufficient number of functional groups to the one or more fullerenes so that the derivatized fullerenes are substantially soluble in a selected solvent. Insoluble non-derivatized or partially derivatized fullerenes and insoluble non-fullerenic carbonaceous material in the starting fullerenic material can be separated from the one or more derivatized soluble fullerenes. After separation from insoluble materials, the one or more derivatized soluble fullerenes can then be treated if desired to remove cyclopropyl adducts and the functional groups that they contain to regenerate the one-or more fullerenes that were initially derivatized in the purification process. This process separates and purifies the one or more fullerenes from other insoluble fullerenes and insoluble non-fullerenic carbonaceous material that is typically present in fullerenic materials, including soot generated in combustion synthesis or arc synthesis.

This invention further provides fullerenes or mixtures of fullerenes that are derivatized by the methods of this invention and/or fullerenes or mixtures of fullerenes that are purified by the methods of this invention. The invention is specifically directed to fullerenes, including endohedral fullerenes, that are derivatized to contain 5 or more, 5-10 or 10 or more cyclopropyl or silacyclopropyl adducts (e.g., >$AR_1R_2$) generated by the methods of this invention.

DETAILED DESCRIPTION OF THE INVENTION

Figure 1:
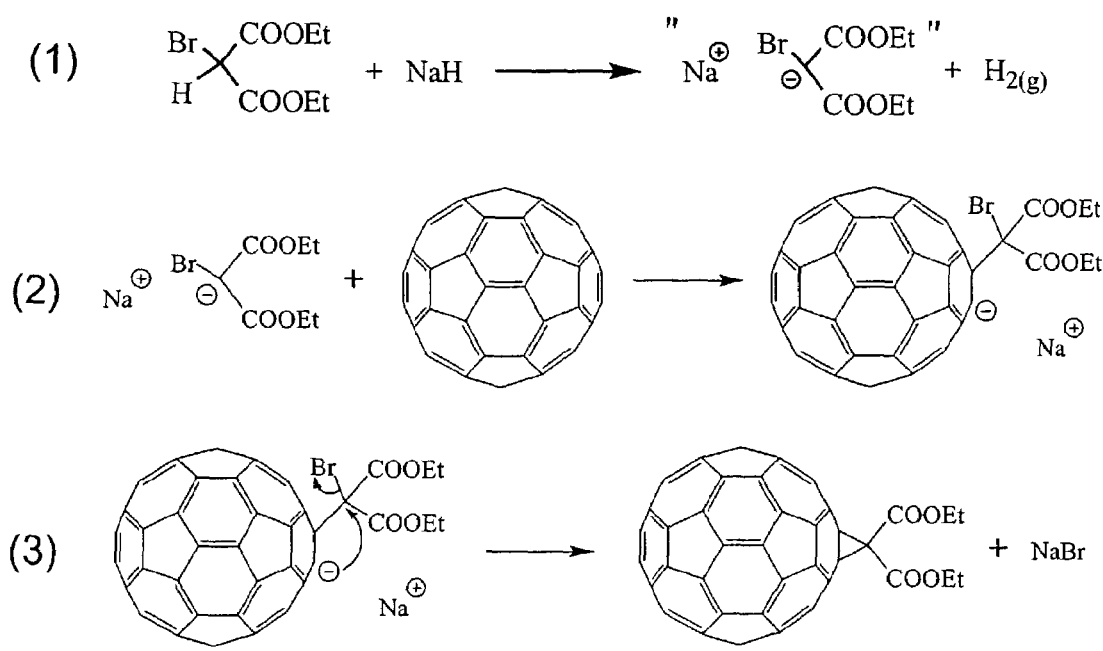
FIG. 1 is a schematic of the Bingel reaction on $C_{60}$.

The term "fullerene" is used generally herein to refer to any closed cage carbon compound containing both six-and five-member carbon rings independent of size and is intended to include the abundant lower molecular weight $C_{60}$ and $C_{70}$ fullerenes, larger known fullerenes including $C_{76}$, $C_{78}$, $C_{84}$ and higher molecular weight fullerenes $C_{2N}$ where N is 50 or more (giant fullerenes) which may be nested and/or multi-concentric fullerenes. The term is intended to include "solvent extractable fullerenes" as that term is understood in the art (generally including the lower molecular weight fullerenes that are soluble in toluene or xylene) and to include higher molecular weight fullerenes that cannot be extracted, including giant fullerenes which can be at least as large as $C_{400}$. Additional classes of fullerenes include, among others specifically noted herein, endohedral fullerenes containing one or more elements, particularly one or more metal elements, and heterofullerenes in which one or more carbons of the fullerene cage are substituted with a non-carbon element, such as B or N. The term fullerenic material is used generally to refer to a material that contains a mixture of fullerenes or a mixture of one or more fullerenes with non-fullerenes, e.g., amorphous carbonaceous materials that may for example be formed during fullerene synthesis by any known method and includes raw or crude preparations of fullerenes, such as combustion soot as well as raw or crude preparations of fullerenes that have been at least partially purified, for example, by extraction and/or sublimation.

Fullerenes are members of a broader class of materials called "carbon nanomaterials" which as used herein generally refers to any substantially carbon material containing six-membered rings that exhibits curving of the graphite planes, generally by including five-membered rings amongst the hexagons formed by the positions of the carbon atoms, and has at least one dimension on the order of nanometers. Examples of carbon nanomaterials include, but are not limited to, fullerenes, single-walled carbon nanotubes (SWNTs), multiple-walled carbon nanotubes (MWNTs), nanotubules, and nested carbon structures with dimensions on the order of nanometers. Carbon nanomaterials may be produced in soot and, in certain cases, carbon nanomaterials may be isolated from the soot or enriched in the soot. Soot produced during the synthesis of carbon nanomaterials, such as fullerenes, typically contains a mixture of carbon nanomaterials which is a source for further purification or enrichment of carbon nanomaterials or which may itself exhibit desired properties of carbon nanomaterials and be useful as an addition to convey those properties. The term "carbon nanomaterials," when used without limitation, is intended to include soot containing detectable amounts of carbon nanomaterials. For example, the term fullerenic soot is used in the art to refer to soot containing fullerenes. Fullerenic soot is encompassed by the term carbon nanomaterials. Non-fullerenic carbonaceous materials include, but are not limited to, non-fullerenic carbon nanomaterials as well as amorphous carbonaceous materials. Carbon nanomaterials are not amorphous carbonaceous materials.

As used herein, "derivatization" generally refers to the chemical modification of a fullerene or the further chemical modification of an already derivatized fullerene. Derivatization of a fullerene refers to the attachment of one or more chemical groups to the fullerene surface. Further derivatization of a derivatized fullerene refers to further attachment of groups to the fullerene surface. The derivatization method of this invention is based in one embodiment on the cyclopropanation reaction as applied to soluble fullerenes first reported by Bingel et. al. and further expanded upon by Hirsch et. al. (Bingel, 1993; Hirsch, 1994(a); Bingel, 1998). In the "Bingel derivatization", base-induced deprotonation of □-halo (halogen: F, Cl, Br, I) substituted bis-malonates and more generally alpha-halo-CH-acids (see U.S. Pat. No. 5,739,376) examples of the "cyclopropanation reagent" as used herein produces an incipient carbanion. This nucleophilic carbanion adds to the fullerene surface, making a new carbon-carbon bond, followed by elimination of the halide anion, completing the cyclopropanation and leaving a neutral derivative group positioned 1,2 across a carbon-carbon double bond of the fullerene. The cyclopropanation reagent of the method of this invention can also be generated in situ by treatment of mono- and bis-malonates and other acids and esters, for example, with halogen-releasing agents such as $CBr_4$, $I_2$, etc. (as described by Camps, 1997; Nierengarten, 1997). This allows for derivatization with more elaborately substituted groups for which the α-halo precursor may be difficult to individually prepare and/or isolate as a reagent. The Camps and Nierengarten references are specifically incorporated by reference herein to provide details including useful halogen-releasing agents and esters and acids of in situ generation of cyclopropanation reagents. Other methods known in the art for the generation of cyclopropanation reagents can be employed in the methods of this invention.

It is unlikely that electron transfer from the carbanion to the fullerene, followed by radical combination, occurs. Nonetheless, the net result would be indistinguishable and thus this mechanism cannot be ruled out in certain cases. Alternatively, a redox-based mechanism could also operate, with the base first donating an electron to produce a fulleride anion, which may have greater solubility in the polar solvent than its precursor neutral fullerene. In the case of radical or open shell $M@C_{2n}$ precursors, such as is the case when trivalent metals are inside $M@C_{60}$ and $M@C_{82}$, the product of a one-electron reduction would be diamagnetic (a molecule having no unpaired electrons) which could act as a stable anionic intermediate in the derivatization process. This fulleride anion may act as the base which deprotonates the substrate, initiating nucleophilic reaction. Experiments have shown that $C_{60}$ can be reduced to its 1- or 2-anions in THF by bases such as NaH. This generally requires a longer reaction time than employed for the cyclopropanation reaction, however. $C_{60}{}^{n-}$ anions were mixed with substrates such as diethylbromomalonate and mass spectrometric analysis of the products indicated multiple cyclopropanations took place, even in the absence of excess NaH (removed after $C_{60}{}^{n-}$ generation). The degree of participation of such a mechanism is difficult to ascertain in the disclosed reactions, but it is likely limited by to the low solubility of the fullerenes and slow kinetics of the formation of reduced species of these fullerenes. Its participation would be mediated by the reducing power of the base in the solvent(s) used.

The final step in the derivatization is the elimination of the neighboring halogen group as a halide anion and closure of the 1,2 bis-addition cyclopropanation. This is the "mechanism" by which derivatization achieves passivation of the insoluble small HOMO-LUMO gap fullerene. The derivatization changes the electronic structure of the fullerene molecule, widening its HOMO-LUMO gap and making it more stable as a free molecule. If the fullerene is intrinsically a radical, for example in the case of endohedral metallofullerenes where the metal donates an odd number of electrons to the cage, derivatization also diminishes the tendency for the molecule to dimerize/oligomerize by sterically shielding the radical, whether it is localized or delocalized on the fullerene cage.

In the present invention cyclopropanation is performed under significantly different conditions from those already reported in the art. The reaction is carried out in a heterogenous mixture (i.e., not a homogeneous solution) in a polar aprotic solvent, preferably in an aprotic solvent that is at least moderately polar and more particularly in an ether solvent, such as tetrahydrofuran, 1,4-dioxane, dimethoxyethane or miscible mixtures thereof. A subset of solvents useful in this invention include non-halogenated polar solvents, including ethers. Additionally, the improved method is rapid, does not require heating of the reaction mixture and it does not require the use of strongly coordinating and reactive bases such as the amine DBU.

As used herein, a "cyclopropanation reagent" is a reagent used to conduct a cyclopropanation or a silacyclopropanation reaction. The cyclopropanation reagent contains at least one cyclopropanation reactive group, i.e., a group within the reagent that participates in and facilitates the formation of a cyclopropyl ring or a silacyclopropyl ring, as used herein particularly on the surface of a fullerene. The cyclopropanation reactive group of the cyclopropanation reagent is a group with a relatively easily removable proton, which upon "removal", leaves a relatively stabilized carbanion, silyl-centered anion or functionally equivalent intermediate nucleophile which can attack the fullerene cage to form the three-member ring. The prototypical substrate is diethylbromomalonate. Other examples include: various halo mono- and bis-malonato compounds, halo-diaryl methanes, and so on (Bingel, 1998). New examples of substrates continue to develop (for example, phosphonates and phosphonic acids; see Cheng, 2000; Pellicciari, 2000; Nuretdinov, 2000), and this brief list is not meant to be all-inclusive (for a review of reactions of stabilized nucleophile substrates with electron deficient alkenes and alkynes prior to the chemistry of fullerenes, see Jung (1991)). Specific cyclopropanation reagents that can be used in the method of this invention are listed in U.S. Pat. No. 5,739,376., the description of these reagents is incorporated by reference herein.

U.S. Pat. No. 5,739,376 at column 4 provides the following description of cyclopropanation reagents having the formula therein of:

wherein $E_1$ and $E_2$ are identical or different and are each COOH, COOR, CONRR$^1$, CHO, COR, CN, P(O)(OR)$_2$ and SO$_2$R, where R, R$^1$ are each a straight-chain or branched aliphatic radical ($C_1$ to $C_{20}$) which may be unsubstituted or monosubstituted or polysubstituted by identical or different substituents, in which radical up to every third CH$_2$ unit can be replaced by O or NR$^4$, where R$^4$ is ($C_1$-$C_{20}$)-alkyl or benzyl, or a benzyl radical or phenyl radical which can be unsubstituted or substituted by from 1 to 5 substituents R, OH, OR, COOR, OCOR, SO$_3$H, SO$_2$Cl, F, Cl, Br, NO$_2$ and CN or together are

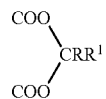

or are different from one another and are each COR, R or H, or are different from one another and are each COR/R or F/Cl/Br, or are different from one another and are each NO$_2$, R$^3$ or H, where R$^3$ can be an unsubstituted, monosubstituted or polysubstituted aliphatic radical ($C_1$ to $C_{20}$), and X is —Cl, —Br, —I, —OSO$_2$Ar, —OSO$_2$CF$_3$, —OSO$_2$C$_4$F$_9$.

At column 3, lines 51-57 of this patent it is stated that:
The straight-chain or branched aliphatic radical ($C_1$-$C_{20}$) R, R$^1$ can be, for example, preferably monosubstituted or disubstituted by identical or different substituents OH, COOH, COOAr, CONR$_2$$^5$ (sic, CONR$^5$$_2$), CONR$^6$, OCOR$^5$, COOCH$_2$Ar, CONHCH$_2$Ar, CONHAr, CONHR$^5$, COOR$^5$, halogen, CONH$_2$, COCH$_2$Ar, COAr, CO ($C_1$-$C_6$)-alkyl or CHO, where Ar, R$^5$ and R$^6$ are as defined above.

and Ar, R5 and R6 are defined (column 3, lines 9-32) as:
Ar is a phenyl radical which can likewise be substituted by from 1 to 3 substituents OH, OMe, Me, CO$_2$R$^1$, OCOR$^1$, SO$_3$H, SO$_2$Cl, F, Cl, Br, NO$_2$ and CN or can be substituted by a straight-chain or branched aliphatic radical ($C_1$-$C_{20}$), preferably $C_1$-$C_{10}$, which may be unsubstituted or monosubstituted or disubstituted by identical or different substituents COOR$^5$, CONHR$^5$, CONR$_2$$^5$, CONH$_2$, CONR$^6$, COOH, OH or OCOR$^5$, COOAr, COOCH$_2$Ar, where R$^5$=

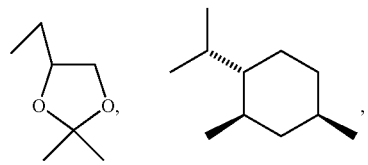

—$C_1$-$C_6$-alkyl, hydroxy-($C_1$-$C_6$)-alkyl, carboxy ($C_1$-$C_6$)-alkyl or ($C_1$-$C_3$)-alkylcarboxyl-($C_1$-$C_6$)-alkyl; and
R$^6$=$C_{11}$-$C_{17}$-alkylene in which up to every 3rd CH$_2$ unit can be replaced by O and which together with the amide nitrogen forms a $C_{12}$-$C_{18}$ ring, and Ar is as defined above.

$E^1$ and $E^2$ are substituents on the cyclopropane derivatized fullerene which derive from the cyclopropanation reagent. Thus, the $E^1$ and $E^2$ definitions beginning at the top of column 2 also relate to $E^1$ and $E^2$ groups on the cyclopropanation reagent. These definitions include:

$E^1$ and $E^2$: are identical or different and are each COOR, COR, P(O)(OR)$_2$, COOH, CN, where R is a straight-chain or branched, aliphatic radical ($C_1$ to $C_{20}$) which may be unsubstituted or monosubstituted or polysubstituted by identical or different substituents, in which radical up to every third CH$_2$ unit can be replaced by O or NR$^4$, where R$^4$=($C_1$-$C_{20}$)-alkyl or benzyl, or a benzyl radical or phenyl radical which can be unsubstituted or substituted by from 1 to 3 substituents R, OH, OR, COOR, OCOR, SO$_3$H, SO$_2$Cl, F, Cl, Br, NO$_2$ and CN, or together are

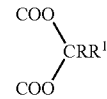

or are different from one another and are each COR, R or H, or are different from one another and are each COR/R or F/Cl/Br where R is as defined above, or are different from one another and are each NO$_2$, R$^3$ or H, where R$^3$ is an unsubstituted, monosubstituted or polysubstituted aliphatic radical ($C_1$ to $C_{20}$)."

Further, in column 3, lines 34-49, of this patent, $E^1$ and $E^2$ groups which are "very Particularly" preferred are described as:
$E^1$/$E^2$: CO2 Alkyl$^1$/CO Alkyl$^1$; CO$_2$Alkyl$^1$/COAlkyl$^2$; COAr/Ar; COAr/Alkyl$^1$; COAr/H, where Alkyl$^1$, Alkyl$^2$ are each a straight-chain or branched alkyl radical having from 1 to 10 carbon atoms in which up to every third CH$_2$ unit can be replaced by O, and Ar is a phenyl group which can be substituted by a straight-chain or branched aliphatic radical ($C_1$-$C_6$) which may be unsubstituted or monosubstituted or disubstituted by identical or different substituents COOR$^5$, CONHR$^5$, CONR$_2$$^5$, CONR$^6$, COOH, OH or OCOR$^5$, where R$^5$ and R$^6$ are as defined above.

Cyclopropanation reagents can also be those which can be used in a tether-directed addition strategy. For a Bingel-style multi-derivatization, a tether-directed addition strategy offers control over regiospecificity of addition (location pattern of the cyclopropanations) and the number of addend groups in a pre-determined way while increasing yields over traditional derivatization strategies, as reviewed by Diederich et. al. (Diederich, F.; Kessinger, R. (1999). "Templated Regioselective and Stereoselective Synthesis in Fullerene Chemistry," *Acc. Chem. Res.*, 32, 537-545). The tether strategy uses multifunctional cyclopropanation reaction groups cojoined in one molecule by covalent linker moieties of variable length separating these functionalities, which are themselves variable in number. The cyclopropanation reactions may be performed with different size tethered cyclopropanation reagents such as cyclo-[n]-octylmalonates with n>3 as well as modified cyclo-species with different length and composition spacers in place of the octyl groups. This can also include tether motifs that link malonates or similar reactive substrate groups with a chemical backbone entirely different from that of a cyclo-[n]-alkyl motif. Linker moieties can include alkyl, alkenyl, or alkynyl groups, ether groups with one or more oxygens and variable carbon chain lengths, cyclic alkyl, alkenyl or alkynyl groups all of which may be substituted, aryl groups (including phenyl, biphenyl, or naphthalene groups which may be substituted), bicyclic or multicyclic organic groups, and porphyrin groups. In general any organic, or inorganic linker groups that provide the desired spacer length and do not interfere with reactivity of the reagent can be employed. This reaction has been demonstrated with $C_{60}$ but is generally applicable to other fullerene classes including: the insoluble $M@C_{60}$ class of $M@C_{2n}$, soluble-as-ions $M_x@C_{2n}$ species, insoluble small-bandgap $C_{2n}$ fullerenes including $C_{74}$, insoluble "giant" fullerenes $C_{2n}$ (where n>50), soluble $C_{2n}$, soluble $M_x@C_{2n}$, and other endohedral fullerenes, metal-carbon nanoencapsulates and carbon nanotubes.

In one embodiment, the cyclopropanation reagent of the method of this invention has the formula:

where A is a C or Si atom;

LG is a leaving group; and $R_1$ and $R_2$ are independently selected from the group consisting of optionally substituted alkyl, alkenyl, alkynyl, or aryl groups, —$COOR_3$ groups, —O—CO—$R_3$ groups, —$COR_3$ groups, —CO—$NR_3R_4$ groups, —O—CO—$NR_3R_4$ groups, —CN, —P(O)($OR_3$)($OR_4$) groups, and —$SO_2R_3$ groups where $R_3$ and $R_4$ are independently selected from hydrogen, or an alkyl group, alkenyl group, alkynyl group or aryl group any of which may be optionally substituted, wherein one or more non-neighboring CH, or $CH_2$ moieties in $R_1$, $R_2$, $R_3$ or $R_4$, can be replaced with an O or S atom and wherein one or both of $R_1$ and $R_2$ contain at least one electron withdrawing or other moiety that stabilizes a negative charge to render the H bonded to A acidic and $R_1$ and $R_2$ optionally contain one or more -AHLG-groups and wherein two or three of $R_1$, $R_2$ or LG may be covalently linked to each other to form one or more rings;

LG can for example be selected from the group —Cl, —Br, —I, and —$OSO_2R$ where R is an optionally substituted alkyl or aryl group. R can for example be substituted with one or more halogens. R can specifically be a fluoroalkyl group, e.g., a perfluoroalkyl group or a fluoroaryl group, e.g., $C_6F_5$, and more specifically R can be a —$CF_3$ group or a —$C_4F_9$ group. A preferred LG is Br.

In specific embodiments, $R_1$ and $R_2$ can be independently selected from the group consisting of —$COOR_3$ groups, —O—CO—$R_3$ groups, —$COR_3$ groups, —CO—$NR_3R_4$ groups, —O—CO—$NR_3R_4$ groups, —CN, —P(O)($OR_3$)($OR_4$) groups, and —$SO_2R_3$ groups where $R_3$ and $R_4$ are as defined above. In more specific embodiments $R_1$ and $R_2$ are both —$COOR_3$ groups.

In other specific embodiments, one or both of $R_1$ and $R_2$ contain one or more cyclopropanation reaction groups, e.g., -A(H)(LG)- where LG is a leaving group that facilitates the desired reaction and LG is more specifically selected from the group from the group —Cl, —Br, —I, and —$OSO_2R$ where R is an optionally substituted alkyl or aryl group. R can for example be substituted with one or more halogens. R can specifically be a fluoroalkyl group, e.g., a perfluoroalkyl group or a fluoroaryl group, e.g., $C_6F_5$, and more specifically R can be a-$CF_3$ group or a-$C_4F_9$ group. A preferred LG is Br.

In other specific embodiments, $R_1$ and $R_2$ are covalently linked together to form a ring. In a more specific embodiment, the covalently linked $R_1$ and R2 groups also contain one or more cyclopropanation reaction groups.

After cyclopropanation, the functional groups attached to the fullerene can be selected from the group consisting of:

>$CR_1R_2$ and >$SiR_1R_2$ where $R_1$ and $R_2$ are as defined above.

In the present invention, multiple groups can be attached to the fullerene during the derivatization process. In different embodiments, the number of groups attached during the derivatization process is more than 5, between 5 and 10, more than 10, and between 10 and 20. For fullerenes with larger cage sizes, greater numbers of groups may be attached to improve solubility. The theoretical limit to the number of groups which can be attached depends upon the cage size of the fullerene. For example, for $C_{2n}$, a maximum of n groups can be attached. In different embodiments, the number of groups attached is up to 0.20*n and between about 0.20*n and 0.75*n.

Cyclopropanation can be employed to introduce functional groups that can be further reacted and converted to other functionalities. In this case $R_1$ or $R_2$ is a group that can be converted into a desired functional group. For example, ester groups introduced by cyclopropanation can be cleaved and converted to other functionalities, effecting side-chain modification (such as in Lamparth, 1997 which is specifically incorporated by reference herein to provide details of such side-chain modifications). For example, the ester groups can be converted to their respective carboxylic acids or carboxylate salts of alkali metals.

Cyclopropanation reagents of particular interest for use in the methods of the present invention include those having the formula:

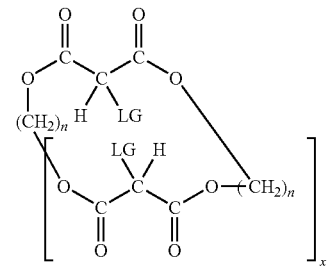

where LG is a leaving group and n and x are integers that are 2 or more. In particular embodiments, the methods herein employ the above reagent where n is 2-20 and x is 1-10; or wherein n is 6-10 or wherein x is 1-5. Preferred LG for this reagent is —Cl, —Br, or —I. Reagents of this formula can be prepared by methods known in the art from readily available starting materials.

Thus in the method of the present invention a solid containing one or more fullerenic species can be combined with the cyclopropanation reagent and a suitable base in the presence of an aprotic polar solvent, particularly an aprotic solvent that is at least moderately polar, forming a dispersion of the solid in the solvent. Other reactants (base and cyclopropanation reagent) may or may not be soluble in the solvent. The solid containing one or more fullerenes is preferably provided in a powdered form, e.g., by application of grinding or other methods to decrease the particle size of the solid. Rapid stirring, optionally with sonication, can suspend the fullerenic species in the solvent and aid in creating a uniform mixture of fullerene, solvent, cyclopropanation reagent, and base. For those fullerenic species that are substantially insoluble in the polar solvent only trace amounts will dissolve in the solvent. Only for those fullerenic species that are slightly soluble will any appreciable amount of starting fullerene be in solution under the conditions of the reaction of this invention. It is recommended that the derivatization reactions be performed in a suitable air-free environment, such as a glove box (dry box) or in glassware with appropriate vacuum/Schlenk line equipment. Use of excess base and excess cyclopropanation reagent over the total molar content of fullerenes present in the sample being derivatized allows the addition of multiple chemical groups to the fullerene surface.

Preferred solvents do not have a readily available acidic proton, and do not contain halogen groups that are chemically reducible by the deprotonating base of choice. Preferred solvents are polar or moderately polar aprotic solvents. As used herein, a "moderately polar solvent" has a dielectric constant greater than or equal to 3. In different embodiments, the solvent has a dielectric constant greater than or equal to 3, greater than or equal to 5, and greater than or equal to 7. Suitable solvents include but are not limited to aliphatic and aryl ethers (e.g. dimethoxyethane, etc.), cyclic ethers (e.g. tetrahydrofuran (THF)), dichloromethane, tetrachloroethane, ortho-dichlorobenzene, more generally halo-benzenes, dimethylsulfoxide, etc. In one embodiment, the solvent is not halogenated. Preferred solvents are pure, dried (free of water), and oxygen free. Without wishing to be bound by any particular theory, the use of polar aprotic solvents is believed to be important for several reasons. First, the incipient carbanion formed by deprotonation of the cyclopropanation reagent is more "stabilized" in polar aprotic solvents than in the non-polar solvents such as benzene, toluene, etc. This increases the nucleophilicity of the incipient carbanion which as a consequence considerably enhances its derivatizing power towards fullerenes. This is confirmed by the ability of the incipient carbanion to derivative fullerenes to any extent in polar aprotic solvents, solvents in which most non-derivatized fullerenes have only marginal to zero solubility.

Useful bases capable of deprotonating the substrate without unnecessarily attacking the fullerene in this procedure are chiefly metal hydrides. Examples include but are not limited to simple alkali hydrides (LiH, NaH, KH, RbH, CsH), alkaline earth hydrides, complex hydrides (LiAlH$_4$, "Red-Al®" Na(CH$_3$OCH$_2$CH$_2$O)$_2$AlH$_2$, etc.), metal borohydride and cyanoborohydride salts, tetraphenylborate salts, lithium acetylide, lithium amides LiNR$_2$ (R=isopropyl (LDA: lithium diisopropylamide); R=triisopropylsilyl; etc.), metal alkoxides, and metal superoxide salts. The choice of base is carefully considered and matched to the respective chosen fullerenes and substrates, as unwanted competing reactions can result. These competing reactions may include nucleophilic addition of base to fullerene, reduction of the fullerene to anionic state(s), and decomposition of the substrates. These side-reactions may occur without significant interference in the production of the final cyclopropanated product. An alternative scheme to the above use of base is to employ sub-stoichiometric levels of coordinating soluble bases (i.e. nitrogen bases; DBU, etc.) in the presence of an excess quantity of a proton scavenger such as commercially available "Proton Sponge" (1,8-bis(dimethylamino)naphthalene) or one of its widely available variants that are strong bases but are weakly nucleophilic for steric reasons. Another modification is to employ appropriate crown ethers and cryptands to enhance solubility of metal-salt bases, e.g. NaH, etc. in the solvents employed. Relevant complexants depend on the size of the metal ion used; for example, K$^+$ ions are well complexed by 1 8-crown-6, dibenzo-18-crown-6, and [2.2.2] cryptand in organic solvents. Addition of these complexants can increase the solubility and reactivity of the base towards deprotonation of the substrate. In general metal hydrides, particularly alkali metal hydride or alkaline-earth metal hydrides are preferred bases for use in the methods of this invention.

These bases typically may have low solubility in the solvents employed, but are highly reactive. For example, immediately upon adding a metal hydride to the stirring mixture of soluble substrate and suspended fullerene in solvent, bubbles due to the evolution of hydrogen are visible. This H$_{2(g)}$ evolves from the combination of the proton and the hydride. Experiments have shown that the base and the malonate can be mixed together in polar aprotic solvent together separately from the fullerene. Evolution of H$_{2(g)}$ is observed, the solution is filtered (Millipore 0.45 µm membrane filter) to remove excess NaH, and the filtrate is added to the fullerene suspension. Rapidly, the solution turns brown as the insoluble fullerene reacts with the carbanion and soluble cyclopropanated fullerene is produced. This demonstration reveals aspects of the reaction mechanism, chiefly that carbanion (formed from deprotonation) can add to the fullerene, forming a new fullerene-substrate bond. Supporting this are the observed reactivity differences between Bingel-Hirsch style reactions of insoluble fullerenes in non-polar solvents and the disclosed reactivity of insoluble fullerenes in polar solvents. Without wishing to be bound by any particular theory, the carbanion in non-polar solvents like toluene may be strongly ion-paired, which reduces its nucleophilicity and significantly diminishes its reactivity with insoluble fullerenes. Conversely, the nucleophilicity of the carbanion is enhanced enough in polar solvents such that it can "attack" insoluble fullerenes efficiently; this is the basis for the disclosed invention.

The methods of this invention for derivatizing insoluble classes of fullerenes have broad utility useful for converting any of the following classes of fullerenic species, among others, to soluble, derivatized species:

1) Insoluble fullerenes which may be intramolecularly polymerized:
   a) Endohedral metallofullerenes insoluble in their native charged state, including but not limited to M$_m$@C$_{2n}$ species such as M@C$_{60}$, M@C$_{70}$, and M@C$_{74}$ where M is one or more metals atoms or ions (the number of metal ions or atoms in the fullerene typically ranges from 1 to about 4 in fullerenes up to about C$_{100}$ but may be higher in larger fullerenes). The insoluble M@C$_{2n}$ endohedral metallofullerenes, whose most prevalent endohedrals of this material are M@C$_{60}$, M@C$_{70}$, and M@C$_{74}$ are further referred to as "M@C$_{60}$ class" metallofullerenes.

Metals that can be contained within the metallofullerene include lanthanide metals, actinide metals, transition metals, alkali metals, and alkaline earth metals. These endohedral metallofullerenes are important as they comprise a major portion of arc-produced metallofullerenes, but due to their polymerized state have heretofore not been usable in promising medical and materials applications requiring dissolution in non-reactive solvents. Water-solubilized metal-containing endohedral fullerenes have important developing applications. Derivatizing Gd@$C_{60}$ represents a significant advance, because of its higher abundance in the arc-produced soot and its potential technological applications. Examples of these applications that will benefit from the derivatization of the more abundant M@$C_{60}$ species in medicinal chemistry include:

1. A contrast-enhancing agent for use in clinical Magnetic Resonance Imaging (MRI). MRI operates by imaging the water protons in vivo using the principles and technology of Nuclear Magnetic Resonance (NMR). When species possessing magnetic spin are introduced, those in proximity to water protons will decrease the relaxation times for those protons ($T_1$ and $T_2$), making them "stand out" relative to those water protons not under the paramagnetic influence. This influence can be outer-sphere or inner-sphere (via direct coordination of water molecules to paramagnetic metal ions). In general, metal ions with high magnetic moments (such as the lanthanide Gd) make the best relaxation agents. However, these ions are toxic if released directly into the bloodstream. Coordination chemistry has been used to minimize free Gd ions while still allowing the complex to act as a MRI relaxation agent. Endohedral Gd fullerenes have an inherent advantage over chelated metal coordination complexes because the endohedral metal is trapped in the interior of the fullerene; there is no equilibrium with an emptied-cage/free metal species. Thus, endohedral fullerenes should be safer in vivo than conventional chelates, from the standpoint of the metal's toxicity. Derivatization introduced by this invention can also be used to link targeting moieties to the fullerene surface.

2. Nuclear medicine agents. Metal chelates of radioactive elements can be used as radiotracers or therapeutic sources of high-energy radioactive decay in vivo. Just like with the above MRI contrast enhancing agents, strong chemical chelators are used to keep the often toxic metal from circulating as a free ion. Also of concern with radionuclides is the potential ejection of the metal from the chelate following the energetic radioactive decay. Endohedral fullerenes will perform better than conventional chelates in both these regards, as the metal cannot dissociate and the cage structure may withstand certain types of decay events and product recoil. This will decrease the deleterious side effects of these nuclear medicine agents to the patient. Derivatization introduced by this invention can also be used to link targeting moieties to the fullerene surface.

b) Empty $C_{2n}$ small-bandgap fullerenes, including but not limited to $C_{74}$, $C_{80}$ ($I_h$ isomer), the newly-discovered $C_{36}$ etc. As used herein, "small bandgap fullerenes" (SBFs) have a HOMO-LUMO gap or band gap that is small (less than about 0.55 eV) or zero. Calculations on the solid-state structure of $C_{74}$ indicate a 2-dimensional network polymer (Okada, 2000), which in the actual materials is probably less than ideally ordered, possibly with some small percentage of soluble $C_{2n}$ species interstitially trapped and/or bonded to other $C_{74}$ molecules. These small-bandgap fullerenes may be produced via the arc process, the combustion process, or by any other process known to those skilled in the art. These fullerenes comprise a subset of fullerenes with special properties, such as reversible redox-controlled depolymerization/polymerization and solid-state conductivity; covalent derivatization will allow for further development of these materials.

2) Insoluble "giant" fullerenes present in fullerenic soot:
 a) Empty fullerenes, including but not limited to, $C_{2n}$ with n approximately greater than or equal to 50. A variable proportion of fullerenic soot produced by different methods (carbon arc, low-pressure combustion, laser desorption, etc.) is made up of these "giant" fullerenes, detected by mass spectrometry but insoluble in known common solvents. Giant fullerene may have a band gap that is small (less than about 0.55 eV) or zero. This insolubility may arise from small-bandgap originated intramolecular polymerization and/or simple size effects, preventing solubility. Derivatization of this class of fullerenes, which are currently discarded as waste materials, will increase the total yield of useable fullerenes from fullerenic soots.
 b) Metal-carbon nanoencapsulates including, but not limited to, 1 mn and larger spherical nanoparticles comprised of a continuous one or more layer graphitic shell encapsulating a nanocrystal of another element, usually a metal or a combination of a metal and one or more other elements. The metal-carbon nanoencapsulates are formed in the arc process under the conditions used to produce metallofullerenes, and in other known processes. This class of materials also includes multi-concentric and/or nested carbon "onions" containing only carbon in their multi-layered structures.
 c) Carbon nanotubes, including but not limited to, single-walled nanotubes (SWNTs) and multi-walled nanotubes (MWNTs). Carbon nanotubes are formed in the carbon arc process as well as other gas-phase procedures, both catalyzed by the presence of transition metals and or other elements. Side-wall derivatization of SWNTs and MWNTs as disclosed herein allows for desirable modification of nanotube properties.

All of the above-listed classes of insoluble fullerenic materials and the related class of carbon nanotubes can be derivatized using the methods of this invention. As noted above derivatization can be employed to increase the solubility or dispersability of a given fullerenic material or of carbon nanotubes in non-polar or polar solvents.

The method of this invention may also be applied to classes of soluble fullerenes, including among others:

Metallofullerenes, including but not limited to, $M_m$@$C_{2n}$ species such as M@$C_{82}$, M@$C_{76}$, M@$C_{84}$ and $M_2$@$C_{80}$, etc. that are soluble in common solvents. Standard fullerene derivatizations already have been reported to derivatize these materials, but the new techniques disclosed herein will also allow them to be derivatized by Bingel cyclopropanation for the first time, and will perform derivatization with greater efficiency than possible before.

Empty $C_{2n}$ fullerenes, including but not limited to, the standard "large-bandgap" fullerenes $C_{60}$, $C_{70}$, $C_{76}$, $C_{78}$, $C_{84}$, etc. and their isomers having solubility in common solvents. Standard fullerene derivatizations already have been reported to derivatize these materials, but the new techniques disclosed herein will allow derivatization with greater efficiency than possible before.

The methods of this invention can further be applied to endohedral fullerenes M@$C_{2n}$ where M represents one or more atoms or ions of any element and wherein when there are multiple M atoms or ions in the fullerene, different atoms or elements ($M_1$, $M_2$, $M_3$, etc.) can be present. Endohedral fullerenes wherein at least one of the M is not a metal atom may be soluble or insoluble. Endohedral fullerenes wherein at least one of the M is not a metal atom are known in the art and can be prepared by methods known in the art.

The methods of this invention can further be applied to heterofullerenes, in which one or more (typically one) carbon of the fullerene cage is substituted with a atom of a non-carbon element, such as N or B.

The methods of this invention can be further applied to fullerenic derivatives made by any known method and particular to those derivatives prepared by any of the methods discussed in this specification. The methods of this invention can be combined in a step-wise fashion with other methods of derivatization of fullerenic species that are known in the art and particularly with methods that are discussed herein to provide variously derivatized fullerenic species.

The functional groups added by cyclopropanation reactions as described herein can be removed by methods known in the art to regenerate underivatized fullerenic species (for example, cyclopropanation is reversible by chemical reduction (Moonen, 2000). Strongly reducing conditions such as amalgamated magnesium and electrochemical reduction at low potentials removes cyclopropanated adducts from fullerenes (Moonen, 2000; Beulen, 2000). In the modified conditions reported here, a soluble reducing agent cobaltocene (CoCp$_2$, Cp=cyclopentadienide; $E°=-1.3$ V vs ferrocene) can be used to perform the retro-Bingel reaction, along with a wide variety of other reducing agents (Reed, 2000).

The generation of soluble derivatives of a given insoluble fullerenic species can be employed to isolate and purify that fullerenic species from other fullerenes or other components of fullerenic soot or enrich the amount of that fullerenic species in a given sample of fullerenic materials. After isolation, purification or enrichment, the functional groups used for solubilization can be selectively removed to provide the underivatized fullerenic species and provide for isolation, purification or enrichment of the non-derivatized material. For example, a derivatization/extraction protocol followed by a defunctionalization step can be used to separate otherwise intractable insoluble fullerenic species, such as "giant" fullerenes, from the soot generated in fullerene production processes. Thus, the invention also provides methods for enrichment, partial purification or purification of one or more insoluble fullerenic species (or carbon nanotubes) in a sample by application of derivatization method of this invention to form one or more soluble derivatives of one or more selected fullerenic species followed by application of separation, partial purification, purification and/or isolation of the derivative or derivatives of the selected species from undesired species in the sample and subsequent removal of derivatives to obtain the selected fullerenic species (or carbon nanotubes) in partially purified, purified or isolated form or to obtain a sample that is enriched in the amount of the selected fullerenic species (or enriched in carbon nanotubes)

The invention provides derivatives of any of the classes of fullerenic species listed above carrying one or more functional groups and in particular provides derivatives of these fullerenic species that are soluble in non-polar solvents, polar solvents and more particularly provides water-soluble derivatives of such fullerenic species. The improved method of this invention produces oxygen and water stable derivatives of fullerenic species from starting materials that themselves lack oxygen and/or water stability and it is highly efficient and adaptable to different classes of fullerenes and reactive substrates, i.e, cyclopropanation reagents.

In a particular embodiment, the derivatized fullerenes of the invention comprise fullerenes selected from the group consisting of empty small band gap fullerenes, M@$C_{60}$ class fullerenes, where M is any magnetic or radioactive metal, giant fullerenes, carbon nanotubes, and metal-carbon nanoencapsulates derivatized with one or more chemical groups selected from the set consisting of >CR$_1$R$_2$ and >SiR$_1$R$_2$ and where R$_1$ and R$_2$ are organic groups independently selected from the set consisting of —COOH, —COOR$_3$, —CO—NR$_3$R$_4$, —CHO, —COR$_3$, —CN, —P(O)(OR$_3$)$_2$, —SO$_2$R$_3$, -and O—CO—N (R$_3$)$_2$ where R$_3$ and R$_4$ are independent selected and are hydrogen, an aryl group, an alkyl group, or an alkenyl group which may be unsubstituted, monosubstituted, or polysubstituted with identical or different substituents selected from the group consisting of —CO, OCO, and N(R$_5$)$_2$, where R$_5$ is hydrogen, an aryl group, an alkyl group, or an alkenyl group, thereby attaching one or more chemical groups to the fullerene surface.

Most importantly, the improved method allows solubilization and/or derivatization and thereby facilitates subsequent utilization of distinct classes of normally insoluble fullerenes which would otherwise be impossible or at best extremely limited solubilization of fullerenic species or carbon nanotubes as derivatives can facilitate separation and purification of such species After purification or separation, functional groups can be removed to provide for insoluble fullerenic species or carbon nanotubes of increased purity. These methods can, for example, be employed to enrich the amount of a selected insoluble fullerenic species or to enhance the amount of carbon nanotubes in a given sample. As one example, the methods of the invention can be used to process small gap fullerenes produced via the combustion process.

Insoluble fullerenes are any fullerenic species generated by any known method which are not soluble in solvents (common solvents, i.e., non-polar organic solvents, such as hydrocarbons and arenes and halogenated arenes, including toluene, benzene) commonly employed to solublize fullerenes, such as $C_{60}$. Solubility (or lack thereof) of a given fullerenic species in a given solvent can be assessed by methods known in the art, e.g., by assessing how much of a fullerenic species can be extracted into a given amount of solvent, for example, using mass spectrometric methods as illustrated herein. The insoluble classes of fullerenes are also insoluble in polar solvents. The methods as described herein can also be applied to those fullerenic species that are substantially insoluble wherein only trace levels of the fullerenic species can be extracted into common solvents. The methods of this invention can also be applied to fullerenic species which are only slightly soluble in common solvents. Non-derivatized fullerenic species are in general not soluble in almost all polar solvents. However, fullerenic species, if soluble have an anomalously high solubility in polar chloro and bromo substituted arenes. As discussed herein and as is understood in the art certain classes of non-derivatized fullerenic species are soluble in non-polar solvents such as toluene and benzene. Thus, the term common solvents is used herein to refer to the non-polar solvents that have typically been found to solubilize non-derivatized fullerenes. The method of the present invention is preferably applied to those fullerenic species either derivatized or non-derivatized, which are insoluble or substantially insoluble in both non-polar and polar solvents as well as to those fullerenic species, either derivatized or non-derivatized, which are insoluble or substantially insoluble in polar aprotic solvents.

The methods of this invention can be used to derivatize insoluble fullerenic species and related carbon nanotube species to make them soluble (or to enhance the solubility of given fullerenic species or carbon nanotubes). Derivatization reaction of this invention may render the derivatized species soluble (or enhance its solubility) in common non-polar solvents or it may render the derivatized species soluble (or enhance its solubility) in polar solvents. For purposes of this application, solubility is defined as the dissolution of free molecules (or salts) in the solvent with reversibility to remove the solvent to obtain the molecules (or salts) dissolved. In preferred cases, the solvent is readily removed by application of reduced pressure and/ or by non-destructive heating. A species may also be removed from solution by recrystallization, for example by addition of solvent in which the species is not soluble to the solution. Certain solvents may readily dissolve a given species, but may not be removable to regenerate the species that was dissolved or it may not be possible to recrystallize the species unchanged. For example, the solvent may only be partially removable or the solvent may have reacted with the species causing a chemical change or irreversible adduct formation. For purposes herein, solubility does not include reaction of the solvent itself with the molecules dissolved to create a new molecule which is then soluble.

In general, fullerenes have "low solubility" in all solvents compared to most organic compounds. For this application, we define relative solubility with the terms soluble, moderately soluble, slightly soluble, substantially insoluble and insoluble on a scale based on the known solubility of fullerene $C_{60}$ in various solvents (See: Ruoff et. al., 1993). $C_{60}$ is insoluble in polar solvents like acetonitrile and methanol (no measurable amount dissolves). $C_{60}$ is substantially insoluble in the polar solvent tetrahydrofuran (~0.001 mg/mL or less). $C_{60}$ is slightly soluble in alkane hydrocarbons (0.002 to 2 mg/mL) and haloalkanes (0.1 to 5mg/mL). $C_{60}$ is slightly soluble to soluble in various arenes (ranging from 1.7 mg/mL in benzene to 27 mg/mL in 1,2-dichlorobenzene). $C_{60}$ is soluble in substituted naphthalenes (30 to 50 mg/mL). The definitions used herein are thus, insoluble approximately 0 mg/mL; substantially insoluble greater than 0 mg/ml and less than or equal to about 0.001 mg/mL (this represents trace amounts); slightly soluble between about 0.002 to about 5 mg/mL; moderately soluble greater than 5 mg/mL and less than about 20 mg/mL; and soluble greater than about 20 mg/mL. As noted above, insoluble classes of fullerenic species are also insoluble in polar solvents. Those classes of fullerenes that are soluble in common solvents (e.g., $C_{60}$) are either insoluble, substantially insoluble or slightly soluble in polar solvents depending on the fullerene in question.

Without wishing to be bound by any particular theory, the insolubility of fullerene species may arise from intramolecular polymerization in certain metallofullerenes ($M@C_{60}$, $M@C_{70}$, $M@C_{74}$, etc. (where M is one or more metals or other elements from the periodic table)) and small-bandgap fullerenes ($C_{74}$, $C_{80}$ ($I_h$ isomer), etc.) or the fullerenes may be too large (i.e., have too high a molecular weight) for effective solubilization (in general, fullerene cages $C_{2n}$ with n approximately greater than 50) such as the "giant" fullerenes which are normally non-extractable from fullerene soot.

Surface derivatization may "passivate" the surface of the otherwise polymerized fullerenes breaking any intramolecular carbon-carbon bonds (removing the covalent bonding to each other) and replacing them with covalent bonds to new surface functional groups. The functional groups can be selected to tune the solubility of the derivatized molecule for different types of solvents and degree of solubilization. The disclosed method for solubilization of normally insoluble fullerenes facilitates the exploitation of their promising medical and technological applications, such as the application of metallofullerenes in nuclear medicine and as contrast agents and the use of fullerene cages as molecular scaffolds for proton transport membranes in fuel cells, etc.

It is believed that the derivatization of polymerized fullerene molecules frees them from an intractable solid-state matrix. Derivatization and/or solubilization of the above species with one or more covalently attached chemical groups can be used to change the properties of these fullerenes and allow for their solution-phase processing, purification and/or separation. The methods herein can further be used for the development of desired properties such as water solubilization, and for the incorporation of chemical handles for the attachment of other groups of biological or other interest (antibodies, proteins, peptides, ligands, drugs, etc.) to fullerenic species.

The disclosed invention represents a significant improvement over the prior art on several different levels. The primary advantage is that it is the first useful exohedral derivatization of the insoluble classes of fullerenes and endohedral fullerenes, including $M@C_{60}$, which are otherwise almost intractable solids as polymerized neutral molecules. This derivatization can be used to impart solubility to these fullerenes so that desired operations such as purification or attachment of technologically important chemical groups can be performed. For example, the disclosed process allows for the first water-solubilization of $M@C_{60}$ species. It is also very significant as the disclosed derivatization allows for the processing and use of $M@C_{60}$ species freely in air for the first time without the interference caused by air/water induced decomposition.

The disclosed procedure for derivatizing fullerenic species has inherent advantages over previous cyclopropanation procedures. It is faster than previous reaction conditions, going to completion in a manner of minutes, and additionally does not require heating of the reaction medium. It is efficiently conducted with insoluble bases, thus allowing the use of nitrogen bases like DBU, etc. to be avoided. Such bases are highly reactive with fullerenes themselves and can interfere with the cyclopropanation of $M@C_{60}$, etc. The reaction conditions are amenable to a wide variety of stabilized carbanions and incipient carbanion intermediates. Cyclopropanation has additional utility because of its reversibility via the "retro-Bingel" reaction, a trait most other fullerene derivatization schemes do not share (including "solvation" with strongly nucleophilic bases like pyridine, aniline, DBU, etc.). The present invention, when applied to combustion-generated fullerenic soot (arc-generated soot or fullerenic soot prepared by other known methods) is distinct from the Diels-Alder chemistry reported by Gügel and Müllen on "giant fullerenes." Their derivatization method is entirely different, with important consequences. A major improvement is the ease of reversibility of the improved derivatization via reductive retro-Bingel reactions (retro-cyclopropanation). This reversibility allows one to use the Bingel-style reaction on the giant fullerenes as a means of extracting them from the amorphous carbon soot as soluble cyclopropanated derivatives, followed by removal of these exohedral groups to re-generate the giant fullerenes as insoluble molecules/polymers. This process selectively removes these desired large fullerene molecules from the amorphous, unordered soot. In this form, the giant fullerenes can then subsequently be derivatized by other desired methods, i.e. hydroxylation, sulfonation, etc. for example, to generate valuable materials for proton-conducting membranes in fuel cells (Hinokuma, 2001(a,b)), without interference from the amorphous soot particles. Using a cyclopropanation/retro-cyclopropanation strategy is also a much more effective way to separate giant fullerenes from soot than is gradient sublimation (Yeretzian, 1993). The cyclopropanation/retro-cyclopropanation strategy can also be applied to related materials such as carbon nanotubes to isolate, purify, or partially purify carbon nanotubes from amorphous materials or to provide samples enriched in carbon nanotubes.

The reactive reagent generated in situ (stabilized α-halo carbanion) is considerably easier to generate than the ortho-quinodimethane precursors needed for the Diels-Alder reactions of Gügel and Müllen, which require multi-step organic syntheses prior to any reaction with fullerenes or soot. The disclosed reaction of carbanions with soot to yield soluble products is considerably faster (minutes) than the Diels-Alder reaction and does not require heating. The Diels-Alder requires reaction at solvent reflux temperature (to extrude the sulfur dioxide from the organic thiophene) for 24 hours or more.

When converted to the water-soluble carboxylic acid and carboxylate salt analogues, the derivatized fullerenes and endohedral metallofullerenes of this invention can be used for medicinal purposes, etc. including MRI contrast enhancing agents and nuclear medicine agents.

When handling the insoluble classes of endohedral fullerenes, it is important to avoid their exposure to the oxygen and/or water present in air. Exposure to air decreases the amount of sublimable endohedral material from the arc process, possibly by forming intramolecular epoxides similar to how $C_{60}$ spontaneously forms $C_{120}O$ in the solid state (Taylor, 1999); the net effect is analogous to an increase in "cross linking" of the fullerene polymer. Air-exposed polymerized fullerenes $C_{74}$ and $M@C_{60}$ can suffer from reduced derivatization reactivity that increases with air exposure time. A method which provides a way to negate the effects of this oxygen and/or water sensitivity so these materials can be used would be particularly valuable. The methods of this invention can be used as a solution to this problem.

The disclosed derivatization procedure has wide application to different classes of insoluble endohedral fullerenes and small HOMO-LUMO gap polymerized fullerenes, as well as the common soluble fullerenes and endohedral fullerenes.

THE EXAMPLES

The following specific examples illustrate the utility of the methods of this invention on different classes of fullerene, but are in no way intended to limit the scope of the invention.

$Gd@C_{60}$ an Insoluble Endohedral Metallofullerene (Insoluble in Both Non-polar and Polar Solvents)

Figure 2:
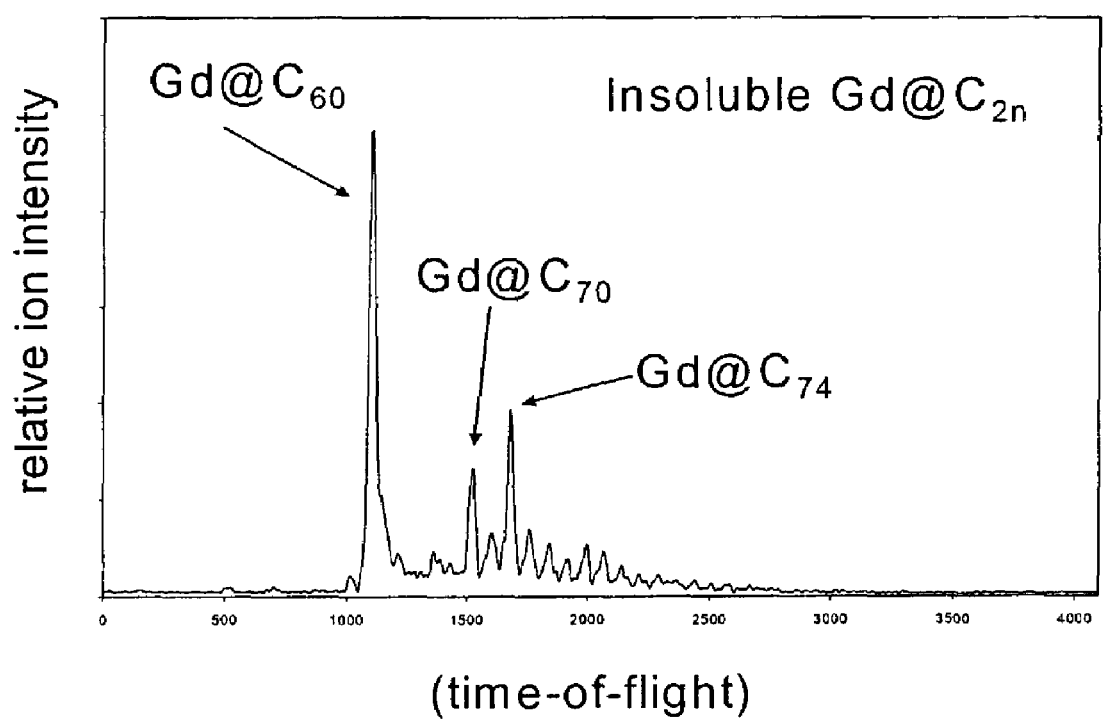
FIG. 2 shows a LD-TOS MS of a fullerene mixture highly enriched in the insoluble classes of Gd@$C_{2n}$ endohedral metallofullerenes.

A LD-TOF MS of a fullerene mixture highly enriched in the insoluble classes of $Gd@C_{2n}$ endohedral metallofullerenes is shown in FIG. 2. The most prevalent endohedrals of this material are $Gd@C_{60}$, $Gd@C_{70}$, and $Gd@C_{74}$. As can be seen, a wide variety of less prevalent other $Gd@C_{2n}$ are also in this material. To simplify discussion, this material will be further referred to as "$Gd@C_{60}$ class" (the most prevalent constituent), recognizing that derivatization reactions done on the $Gd@C_{60}$ component may also be performed on the other components as well.

Solid powder consisting of highly enriched $Gd@C_{60}$ class material was obtained from soot generated from arcing of Gd-impregnated graphite rods in a custom-built carbon-arc style reactor. The resultant soot is sublimed under vacuum at 750° C. overnight. Sublimed fullerenes $C_{2n}$ and endohedral metallofullerenes $Gd_m@C_{2n}$ collect inside the reactor on a chilled coldfinger and are harvested anaerobically inside a glovebox. The soluble fullerenes are then maximally removed from this "sublimate" by solvent extraction. A continuously cycling Soxhlet extractor is used, in combination with a custom built vacuum/cooling condenser that allows for the cycling of ortho-dichlorobenzene at a pressure of about 40 torr and at a temperature of about 100° C. This powerful fullerene solvent removes most of the soluble $C_{2n}$ and $Gd_m@C_{2n}$ over the course of several days of cycling extraction. Next, certain $C_{2n}$ and $Gd_m@C_{2n}$ are removed via oxidative extraction (See: U.S. provisional application No. 60/326,307 "Purification of Endohedral and other Fullerenes by Chemical Methods", filed Oct. 1, 2001 and U.S. application Ser. No. 10/263,374 "Purification of Endohedral and other Fullerenes by Chemical Methods", filed Oct. 1, 2002). The remaining insoluble material is composed of endohedral fullerenes, chiefly $Gd@C_{60}$, $Gd@C_{70}$, $Gd@C_{74}$, and insoluble empty fullerenes, chiefly $C_{74}$, as shown in FIG. 2 above. After hexane rinse and vacuum drying, this material is ready for derivatization. It contains approximately 25%-50% Gd-containing endohedral fullerenes by weight, with the remainder being empty fullerenes (chiefly the SBF $C_{74}$) and residual ortho-dichlorobenzene solvent.

The reaction procedure is conducted inside of the glovebox. $Gd@C_{60}$-containing powder s (100 mg, estimated to be ~1.1×10$^{-4}$ moles of $Gd@C_{60}$ using a molecular weight of approximately 900 g/mole) is stirred vigorously in 5 ml dried tetrahydrofuran (THF). Excess diethylbromomalonate (200 mg, 8.3×10$^{-4}$ moles) is added; the mixture is stirred for 5 minutes. Next, excess solid KH (50mg, 1.3 ×10$^{-3}$ moles) is added while stirring rapidly. Within several seconds, bubbles from the evolution of $H_{2(g)}$ are visible, and within 5 minutes the dark brown color of derivatized fullerene is observed in solution. The reaction mixture can be stirred for as little as 15 minutes; usually it is stirred for 1.5 hours to allow for maximum reaction yield, but this is not required. Then the stirring is halted, the unreacted portion of the fullerenes and KH is allowed to settle, and very dark-brown solution is decanted away. This solution is passed through a 0.45 μm Millipore membrane filter and the THF solvent is removed under vacuum. The product is analyzed by LD-TOF MS (from a sulfur matrix) showing the addition of ca. 9 to 10 diethylmalonate groups, giving a formula of approximately $Gd@C_{60}$ $(C(CoOCH_2CH_3)_2)_x$, x≅9-10 (see FIG. 3). There may be oxygen groups present as epoxides on the surface of the derivatized fullerene arising from unavoidable reaction of the $Gd@C_{60}$ starting material with trace amounts of $O_2$ during its manufacture and storage in the glovebox. This derivative now has solubility in a variety of common polar and non-polar organic solvents.

This derivatized metallofullerene, $Gd@C_{60}(C(COOCH_2CH_3)_2)_x$, can be converted to a water-soluble species by de-esterification to carboxylic acid or carboxylate salt groups. This is performed by the method of Hirsch (Lamparth, 1994). The ester derivative (100 mg) is dissolved in toluene (15 mL) and vigorously stirred at reflux with excess solid NaH (100 mg) under argon for 2-3 hours. Next, methanol (3 mL) is added with stirring. Vigorous bubbling is observed, followed by precipitation of the sodium carboxylate salt of the $Gd@C_{60}$ derivative. The solid is isolated, dissolved in water, and partially purified with dialysis tubing (MW cutoff~500). The water is removed from an aqueous solution of the carboxylate with a rotary evaporator connected to a vacuum source; it is important to avoid decarboxylation by heating gently (<50° C.). Lowering the pH of aqueous solutions of the carboxylate salt can produce the acid form, which may have less water solubility depending on the number of acid groups present. Aqueous-phase size-exclusion chromatography (SEC-HPLC) indicates that the Gd@$C_{60}$(C(COONa)$_2$)$_x$ molecules are not clustered in large aggregates. Ion-exchange resin (Dowex-50, etc. etc.) can be used to change the counterion in Gd@$C_{60}$(C(COONa)$_2$)$_x$ to other alkali metals etc. or to hydrogen (proton) i.e. Gd@$C_{60}$(C(COOH)$_2$)$_x$.

Significantly, the derivatized M@$C_{60}$ materials Gd@$C_{60}$(C(COOCH$_2$CH$_3$)$_2$)$_x$, Gd@$C_{60}$(C(COONa)$_2$)$_x$, and Gd@$C_{60}$(C(COOH)$_2$)$_x$ are all air-stable, showing no evidence for decomposition in the presence of oxygen and/or water over several months time, as indicated by long-term stability of their solutions (lack of precipitation and reproducible spectroscopy) and complete re-dissolution of air/water exposed solids.

Figure 3:
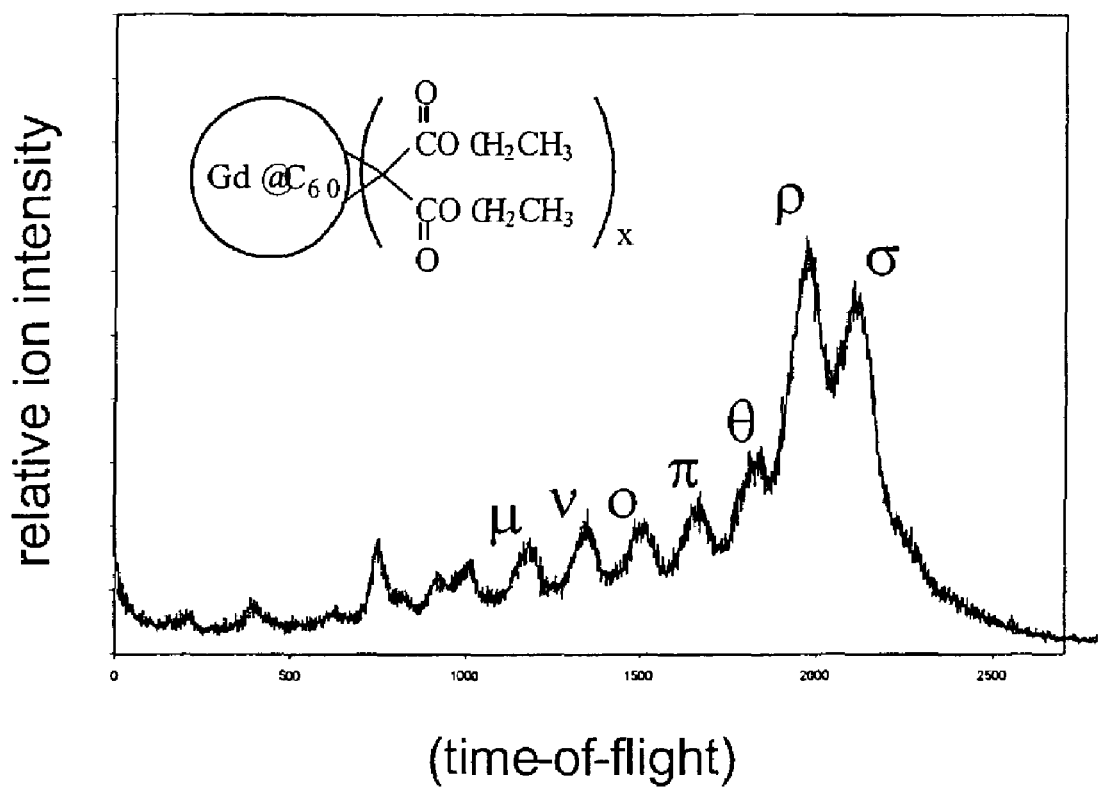
FIG. 3 shows a LD-TOF MS of derivatized Gd@$C_{60}$, Gd@$C_{60}(C(COOCH_2CH_3)_2)_x$.

The mass spectrum in FIG. 3 reveals Gd@$C_{60}$ derivatized by Bingelation reaction with diethylbromomalonate according to this described invention to be Gd@$C_{60}$(C(COOCH$_2$CH$_3$)$_2$)$_x$, with x peaking around 9 to 10 (due to the dominance of Gd@$C_{60}$, derivatized products of the other species, i.e. Gd@$C_{70}$, etc. cannot be discerned by this analysis). Different preparations have slightly different amounts of the higher number of addends, and the MS-detected lower adducts (x=2, 3, 4, 5, etc.) are likely the result of fragmentation by the desorbing laser.

The infrared spectrum (FTIR) of Gd@$C_{60}$(C(COOCH$_2$CH$_3$)$_2$)$_x$ confirms the presence of ethyl ester and carbonyl groups (C—H, 2925 cm$^{-1}$; C=O, 1743 cm$^{-1}$) on the fullerene's surface. This derivative was converted to the fully water-soluble species Gd@$C_{60}$(C(COONa)$_2$)$_x$ via a deesterification procedure. FTIR spectroscopy of this material shows changes in the spectrum expected for conversion of a carboxyl ester to an alkali metal carboxylate salt (loss of C—H; C=O, 1592 cm$^{-1}$).

Of note is the number of groups added to the exohedral surface of the Gd@$C_{60}$ molecules, for example, in FIG. 3 the maximum is ~9 to 10 Bingel groups added. In comparison, using standard Bingel conditions on empty $C_{60}$, generally 6 groups are added to the $C_{60}$ surface, disposed in an octahedral pattern that minimizes steric interactions. The reason for the increase in number of added groups to M@$C_{60}$ as opposed to $C_{60}$ may be due to the inherent electronic characteristics of the M@$C_{60}$ species (affecting the extent of derivatization) and/or the particular modified reaction conditions allowing for increased derivatization extent. There may be oxygen groups present as epoxides on the surface of the derivatized fullerene arising from unavoidable reaction of the Gd@$C_{60}$ starting material with trace amounts of $O_2$ during its manufacture and storage in the glovebox.

Tm@$C_{60}$, an Endohedral Metallofullerene Soluble as an Ion

Tm@$C_{60}$ was derivatized with diethylbromomalonate according to this invention. The reaction was performed starting with a soluble form of the endohedral metallofullerene. A small number of lanthanide M@$C_{60}$ species are soluble in moderately polar organic solvents as free cationic species, e.g. M@$C_{60}^+$, generated by oxidative extraction from sublimates (See, U.S. provisional application No. 60/326,353 filed Oct. 1, 2001 and concurrently filed U.S. application Ser. No. 10/263,374 "Purification of Endohedral and other Fullerenes by Chemical Methods", filed Oct. 1, 2002, which is incorporated by reference in its entirety herein). This oxidative extraction was used as an enrichment/purification procedure prior to the derivatization reaction, but it is not required for the derivatization reaction to be successful. Cationic species formed by the oxidative extraction of M@$C_{60}$ have been found to be moderately soluble in polar solvents and in some moderately polar solvents. Despite the chemically reducing environment of the disclosed reaction conditions, the derivatization of soluble Tm@$C_{60}^+$ species proceeds in an identical manner as with insoluble Gd@$C_{60}$, etc. The disclosed procedure also works to derivatize Tm@$C_{60}$ etc. present in the Tm@$C_{2n}$ material which is not extractable under oxidative conditions, further illustrating its utility for derivatizing insoluble M@$C_{60}$ etc. analogous to the Gd@$C_{60}$ compounds discussed in the section above. Other lanthanide M@$C_{2n}$ probably in the same class as Tm@$C_{2n}$ include Sm, Yb, Eu and possibly Er. Other M@$C_{2n}$ which can be chemically or electrochemically reduced to an anion $M_n$@$C_{2n}^{x-}$ or chemically or electrochemically reduced to a cation $M_n$@$C_{2n}^{X+}$ are also amenable to derivatization. For example, Gd@$C_{60}^-$ can be derivatized.

$C_{74}$ an Insoluble Empty "Small Bandgap" Fullerene (Insoluble in Both Non-polar and Polar Solvents)

Figure 4:
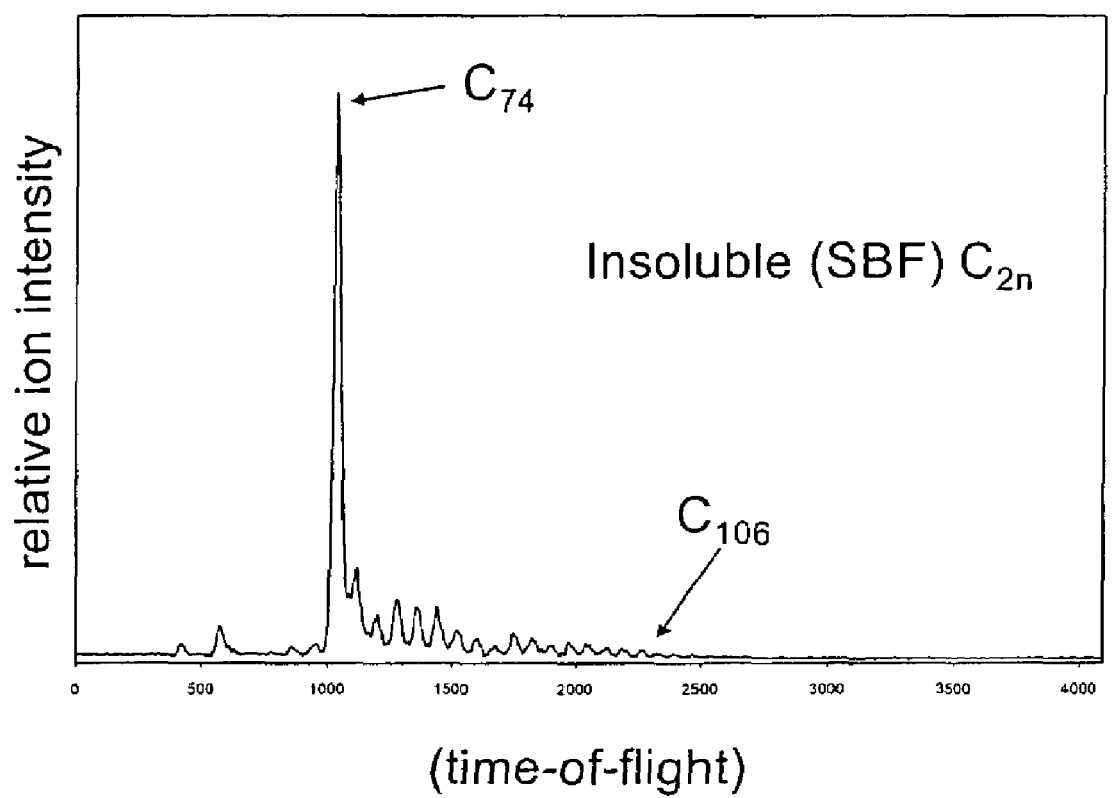
FIG. 4 shows a LD-TOF MS of solvent-washed $C_{74}$ and $C_{2n}$ insolubles.

A fullerene mixture highly enriched in $C_{74}$ and small amounts of larger-cage small HOMO-LUMO gap fullerene isomers was prepared by repeated washing of a mixed empty arc fullerene sublimate with the organic solvent ortho-dichlorobenzene. This washing was most efficiently performed with a continuously automatic cycling soxhlet extractor. It effectively extracted the majority of the soluble fullerenes, resulting in the material as characterized by mass spectrometry shown in FIG. 4.

Figure 5:
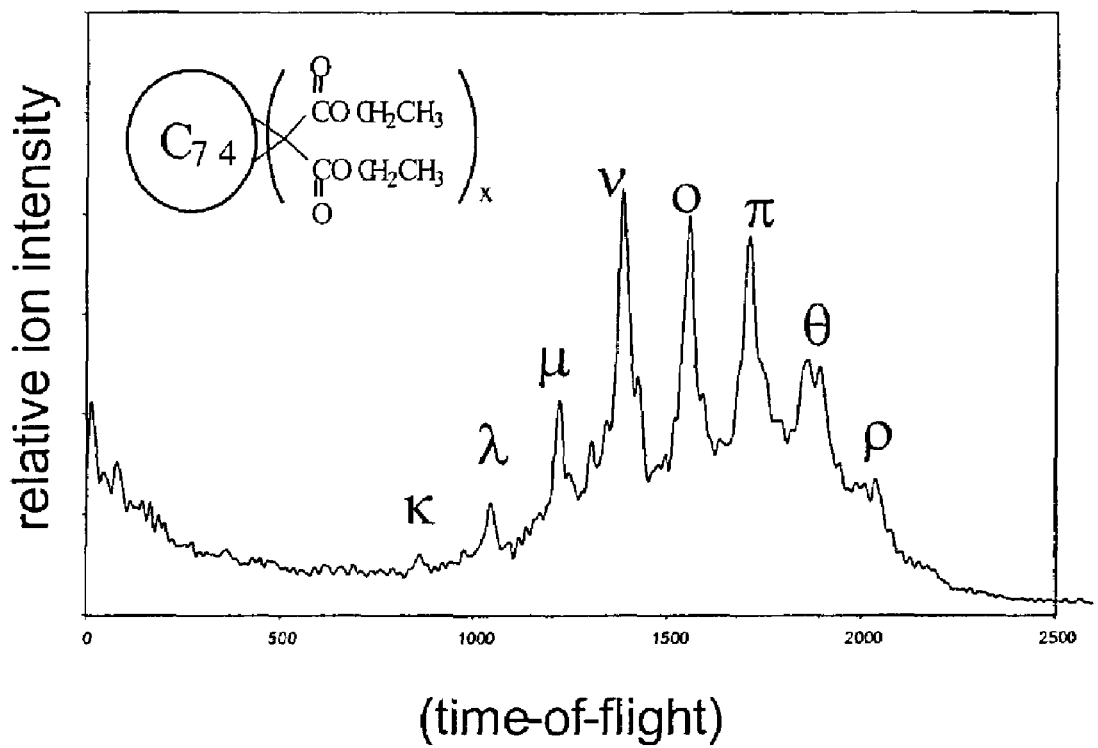
FIG. 5 shows a LD-TOF MS of $C_{74}$ derivatization products $C_{74}(C(COOCH_2CH_3)_2)_x$.
Figure 6:
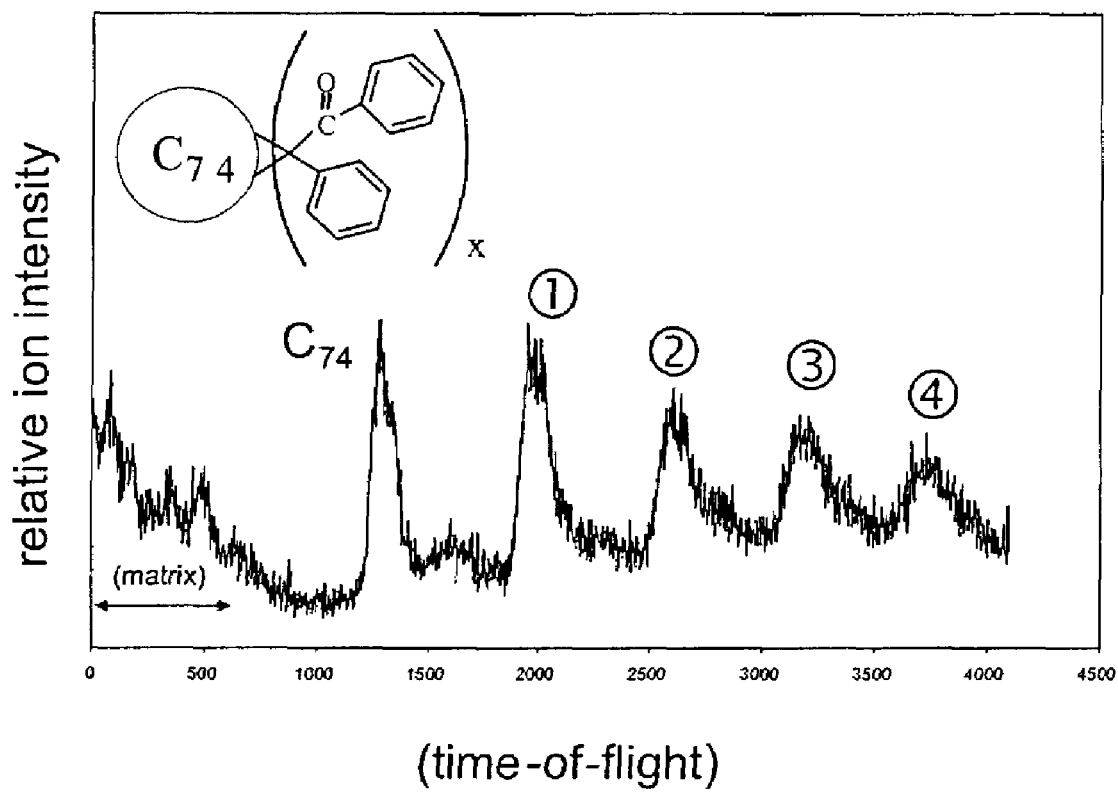
FIG. 6 shows a LD-TOF MS of $C_{74}$ derivatization products $C_{74}(C(COPh(Ph))_2)_x$.

This material, dominated by $C_{74}$, was subjected to reaction under modified Bingel-type conditions as reported above for Gd@$C_{60}$. Substrates added to the $C_{74}$ surface in this manner include diethylbromomalonate forming $C_{74}$(C(COOCH$_2$CH$_3$)$_2$)$_x$ (FIG. 5) and desyl bromide (2-bromo-2-phenylacetophenone) forming $C_{74}$(C(COPh(Ph))$_2$)$_x$ (FIG. 6) as shown by LD-TOF MS on the reaction products.

Insoluble "Giant" Fullerenes Present in Fullerene Soot (Insoluble in Non-polar and Polar Solvents)

Low-pressure combustion-produced fullerenic soot contains a mixture of soluble fullerenes, insoluble small-bandgap fullerenes, insoluble "giant" fullerenes (which likely exist as a wide mixture of structural isomers with different magnitudes of HOMO-LUMO gaps), graphitic soot resembling partially constructed fullerenes, non-fullerenic graphitic and amorphous soot particles and polycyclic aromatic hydrocarbons (PAHs). Fullerene soots generated by other methods, for example the arc method, are similar in composition, but with varying proportions of constituents. The soluble components, fullerenes $C_{2n}$ (with 2n ≦ approximately 100) and PAHs, can be removed by solvent extraction with xylene or other solvents. The remaining insoluble soot solids contain a significant amount of "giant" fullerenes, which in order to be used in technological applications need to be removed from this soot matrix.

Fullerenic soot was produced under standard low-pressure combustion conditions. All freely soluble components (large-bandgap fullerenes $C_{2n}$ where 2n=60, 70, 76, 78, 84, etc. and polycyclic aromatic hydrocarbons) were first removed under conventional solvent extraction conditions. The remaining insoluble soot solids contain a significant amount of "giant" fullerenes (with n approximately ≧ 50) and the small-bandgap fullerene $C_{74}$ (and other small-bandgap $C_{2n}$ with n≦50) mixed in with non-fullerene carbon materials including graphitic soot resembling partially constructed fullerenes, non-fullerenic graphitic and amorphous soot particles. The "giant" fullerenes (with approximately≧50) and the small-bandgap fullerene $C_{74}$ (and other small-bandgap $C_{2n}$ with n≦50) can be selectively separated from the non-fullerene carbon materials by reaction under the disclosed cyclopropanation reaction conditions, effecting them soluble in solvents and removing them from the insoluble, unreacted non-fullerene carbon materials by filtration. The soluble, derivatized "giant" fullerenes (with approximately≧50) and the small-bandgap fullerene $C_{74}$ (and other small-bandgap $C_{2n}$ with n≦50) can be used as derivatized for further applications if desired, or can be re-generated as an underivatized mixture of insoluble fullerene molecules by removal of the derivative groups.

Figure 7:
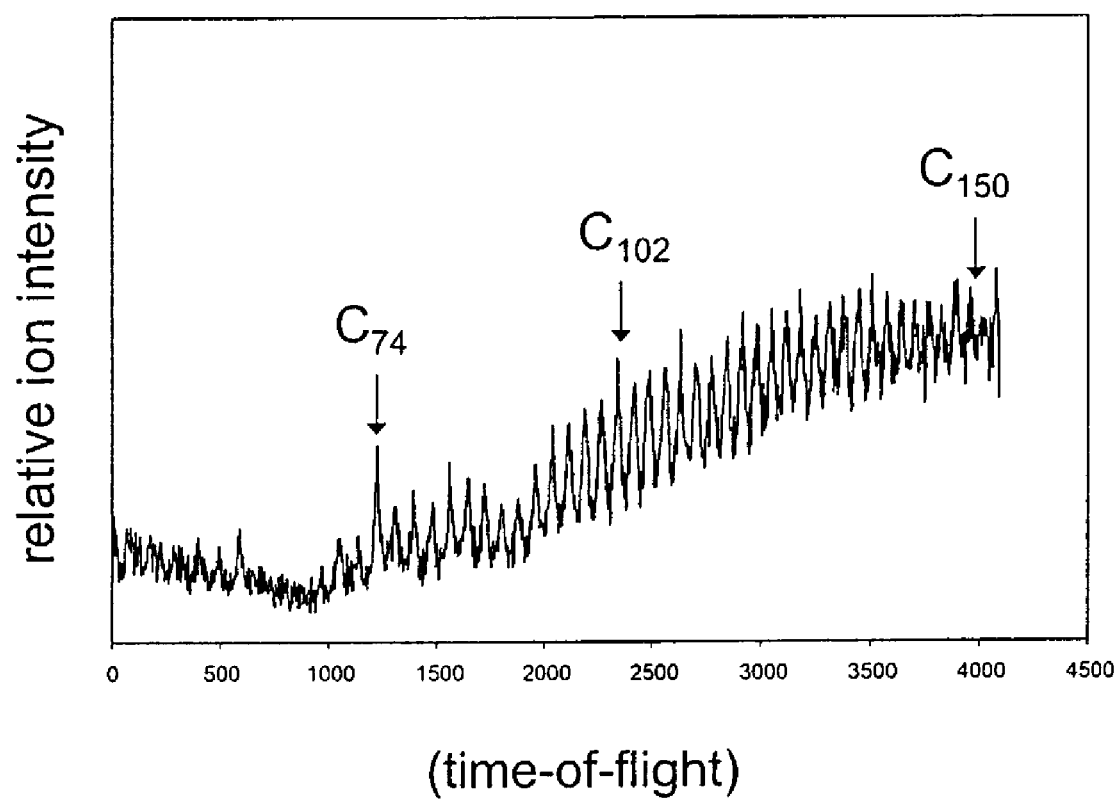
FIG. 7 shows a LD-TOF MS of solvent-washed combustion fullerene soot.

Removal of "giant" fullerenes from the insoluble soot matrix can be effected by the disclosed invention. FIG. 7 shows a LD-TOF MS of a typical insoluble soot material obtained by low pressure flame combustion synthesis of fullerenes. This material has had the soluble fraction removed by continuous solvent extraction with ortho-xylene. Clearly visible is a wide range of large fullerenes along with lesser amounts of smaller fullerenes, including the insoluble SBF $C_{74}$. Arc-produced fullerene soot has similar characteristics as seen with mass spectrometry, but can have higher proportions of $C_{74}$ relative to the other SBFs. Insoluble graphitic soot resembling partially constructed fullerenes, non-fullerenic graphitic and amorphous soot particles do not show up in the LD-TOF MS of FIG. 7 because of their large molecular weights and/or resistance to generation of their gas phase ion(s).

The mixed combustion-produced fullerenic soot (as in FIG. 7, depleted of soluble species as above) is subjected to the disclosed derivatization reaction conditions. 100 mg of mixed combustion-produced fullerenic soot is suspended in 10 mL dry tetrahydrofuran with rapid stirring inside of the glovebox. 200 mg of diethylbromomalonate is added with stirring ($8.3 \times 10^{-4}$ moles), followed by addition of 50 mg of KH ($1.3 \times 10^{-3}$ moles). Rapid evolution of gaseous hydrogen is observed concurrently with the formation of a very dark brown solution. This solution contains cyclopropanated "giant" $C_{2n}$ fullerenes (with n approximately≧50) and the small-bandgap fullerene $C_{74}$ (and other small-bandgap $C_{2n}$ with n≦50), which have now attained solubility. They are separated from the remaining insoluble soot (non-fullerene carbon materials) and unreacted solid KH by filtration through a Millipore 0.45 µm membrane filter or equivalent filtration apparatus. LD-TOF MS of these soluble derivatives reveals a broad continuum of high-mass species, unresolvable as individual ion signals likely due to the incredibly diverse mixture of species and their complicated, overlapping fragmentation patterns. The mixed, derivatized, solubilized "giant" fullerenes (with n approximately≧50) and the small-bandgap fullerene $C_{74}$ (and other small-bandgap $C_{2n}$ with n≦50) molecules can then be isolated as a microcrystalline solid by removal of the tetrahydrofuran solvent by application of reduced pressure, for example.

Because the starting ratio of the "giant" fullerenes (with n approximately≧50) and the small-bandgap fullerene $C_{74}$ (and other small-bandgap $C_{2n}$ with n≦50) to the non-fullerene carbon materials in the starting soot is unknown, the percent yield of derivatized "giant" fullerenes (with n approximately>100) and the small-bandgap fullerene $C_{74}$ (and other small-bandgap $C_{2n}$ with n<100) can not be determined.

Figure 8:
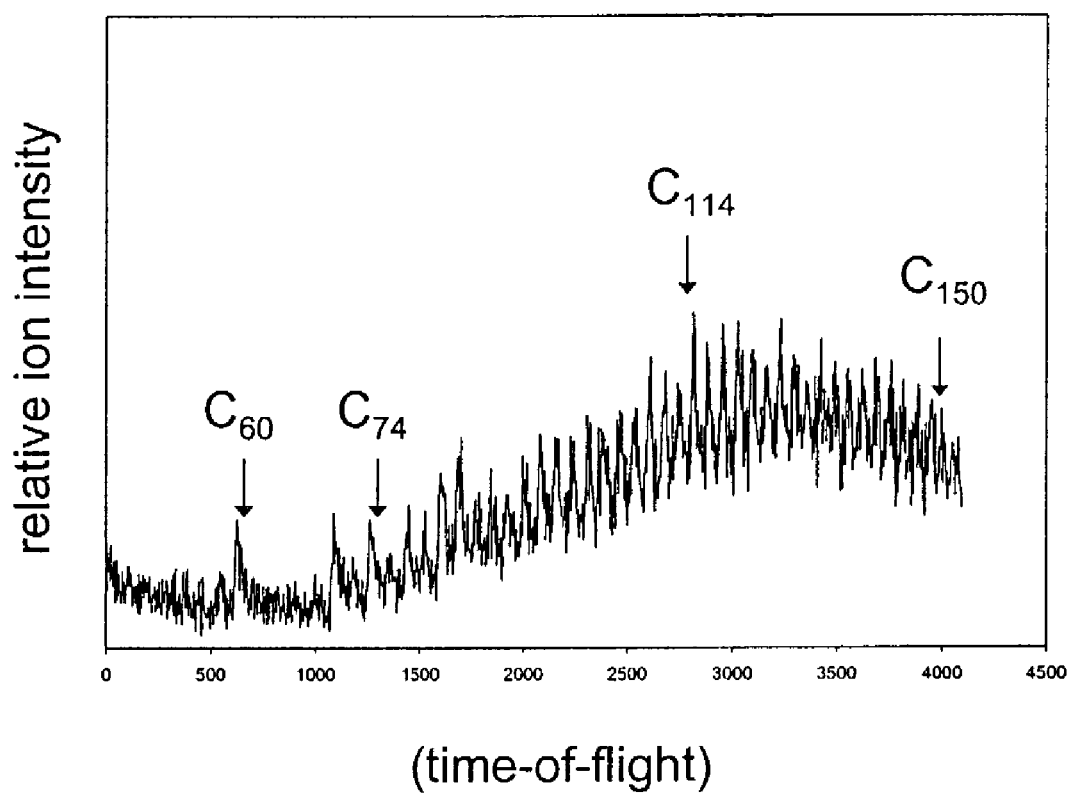
FIG. 8 shows a LD-TOF MS of giant fullerenes that have been un-derivatized after solubilization and filtration.

When desired, a mixture of un-derivatized "giant" fullerenes (with n approximately≧50) and the small-bandgap fullerene $C_{74}$ (and other small-bandgap $C_{2n}$ with n≦50) can be generated by removal of the adduct groups. This is effected by a modified retro-Bingel reaction similar to that of Echegoyen and co-workers (Moonen, 2000; Beulen, 2000). In the modified conditions reported here, a soluble reducing agent cobaltocene ($CoCp_2$, $Cp^- $=cyclopentadienide; $E° = -1.3$ V vs ferrocene) was used to perform the retro-Bingel reaction on the giant fullerenes. 50 mg of mixed "giant" fullerenes (with n approximately≧50) and the small-bandgap fullerene $C_{74}$ (and other small-bandgap $C_{2n}$ with n≦50) is dissolved in 10 mL tetrahydrofuran with stirring (in the glovebox in the absence of oxygen and water, etc. and with dry, purified solvent, etc.). The number of moles is undetermined because of the mixture nature of this material; it is certainly equal to or less than $1 \times 10^{-4}$ moles of fullerenes. 200 mg solid $CoCp_2$ ($1 \times 10^{-3}$ moles) is added with stirring. A precipitate of mixed underivatized "giant" fullerenes (with n approximately≧50) and the small-bandgap fullerene $C_{74}$ (and other small-bandgap $C_{2n}$ with n≦50) forms and is separated by filtration. This solid is washed with acetonitrile and hexanes to remove any unreacted $CoCp_2$. FIG. 8 displays the LD-TOF MS of the solid product, a wide-ranging distribution of "giant" fullerenes (with n approximately>100) and the small-bandgap fullerene $C_{74}$ (and other small-bandgap $C_{2n}$ with n<100) that have been separated from the insoluble, non-fullerenic carbon materials present in combustion soot. Following the net purification process described above, the giant fullerenes of FIG. 8 are now suitable for subsequent further derivatization of their surface, for example to introduce proton-transporting groups (hydroxyls, sulfonates, phosphonates, etc.) for their usage in proton conductive membranes of fuel cells (Hinokuma, 2001 (a, b)). Purified giant fullerenes are then also amenable for use in other developing technological applications of fullerenes.

Important to note is the fact that all the fullerenes in FIG. 8 were previously soluble as derivatives and passed through a Millipore 0.45 µm membrane filter without impediment. This indirectly demonstrates their intermediate derivatization status despite the unavailability of resolved mass spectra for the derivatized mixture. Following the net purification process described above, the giant fullerenes of FIG. 8 are now suitable for subsequent further derivatization of their surface, for example to introduce proton-transporting groups (hydroxyls, sulfonates, phosphonates, etc.) for their usage in proton conductive membranes of fuel cells (Hinokuma, 2001(a, b)). Purified giant fullerenes are then also amenable for use in other developing technological applications of fullerenes.

Gd-containing Metal-Carbon Nanoencapsulates (Insoluble in Non-polar and Polar Solvents)

Metal-carbon nanoencapsulates (MCNs) are nanometer and larger particles consisting of a multi-layer fullerene-like carbon coating surrounding an interior metal nanocrystal (McHenry, 2000). MCNs are produced along with endohedral metallofullerenes in the carbon arc synthesis. The outer surface of MCNs is very similar to the insoluble giant fullerenes (above) and thus is similarly derivatized. Derivatization will be important for developing technological applications of MCNs, because it will allow solubilization, chromatographic size separation, etc.

Gd-containing MCNs were produced in an arc reactor using Gd-impregnated graphite rods, separated magnetically from the soot product, and characterized by electron microscopy, revealing a distribution of different sized MCNs (1-25 nm diameter). These Gd-MCNs, subjected to the disclosed reaction conditions for cyclopropanation with diethylbromomalonate, are shown with solid-state FTIR spectroscopy to have the cyclopropanated groups attached to the outer MCN surface. These groups then can serve as attachment points for linking solubilizing groups, bio-active directing groups (proteins, peptides, antibodies, etc.) and so on. MCNs will have applications as potent MRI contrast enhancing agents, vehicles for encapsulated delivery of radionuclides in vivo, and as nanoscale units of magnetic metals for ferrofluid and magnetic data storage applications (McHenry, 2000). The derivatization of other large, insoluble carbon materials such as nested onion carbon nanoparticles and carbon nanotubes proceeds in a similar manner to the derivatization of MCNs.

Carbon Nanotubes (Insoluble in Non-polar and Polar Solvents, These Materials Can be Dispersed in Solvents with Sonication and the Use of Surfactants)

A commercially obtained sample of SWNTs (single-walled nanotubes) is reacted under modified Bingel-type conditions as reported above for Gd@$C_{60}$ with diethylbromomalonate. Infrared spectroscopy of the reaction product reveals the presence of cyclopropanated adduct groups attached to the side-wall SWNT surface. The covalent addition products are stable in air and in the presence of water. The derivatization protocol works on SWNTs, MWNTs, nanotubes of varied diameters, and both natural length and chemically shortened nanotubes. The method of this invention can be applied to nanotubes produced by different production methods (carbon arc methods, HiPCO processes, etc.). The derivatized carbon nanotubes can be chemically manipulated, cross-linked to one another through their derivative groups, etc.

Gd@$C_{82}$, a Typical Soluble Endohedral Metallofullerene (Slightly Soluble in Polar and Non-polar Solvents)

Gd@$C_{82}$ is representative of the soluble endohedral $M_m$@$C_{2n}$ species commonly available in small quantities. It can be derivatized according to the disclosed process, forming by reaction with diethylbromomalonate Gd@$C_{82}$(C(COOCH$_2$CH$_3$)$_2$)$_x$. This material is also of interest as an MRI contrast enhancing agent (Zhang, 1997; Wilson, 1999; Mikawa, 2001). Other soluble $M_m$@$C_{2n}$ similarly derivatizable include $M_2$@$C_{80}$ species, $Sc_3$@$C_{2n}$ species, $M_3N$@$C_{2n}$ and related species (e.g. $Sc_3N$@$C_{2n}$, $ErSc_2N$@$C_{2n}$, etc.).

$C_{60}$, the Prototypical Soluble Fullerene (Soluble in Non-polar Solvents, but Substantially Insoluble in Polar Solvents)

Figure 9:
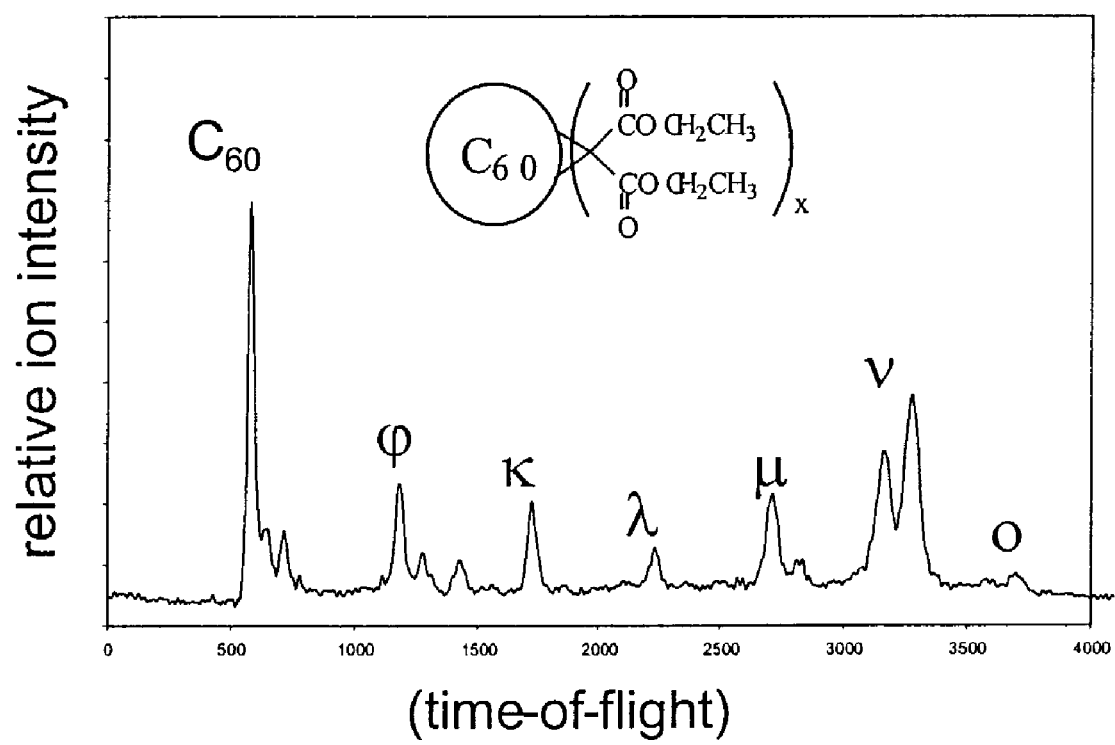
FIG. 9 shows a LD-TOF MS of empty $C_{60}$ derivatization products $C_{60}(C(COOCH_2CH_3)_2)_x$

FIG. 9 shows the TOF-MS of empty $C_{60}$ that has been derivatized according to the standard conditions of this invention disclosure with diethylbromomalonate. Using excess quantities of reagents, the reaction tends to go to completion at 6 or 7 cyclopropanations (methanofullerene adducts).

Additon of Tethered Cyclopropanation Reagents

The current invention can be used to improve on the attachment of multi-functional "tether" reagents to fullerenes. Advantages conferred may include increased yield, decreased reaction time, decreased reaction temperature and lower cost.

The tether compound cyclo-[3]-octylmalonate $C_{33}H_{54}O_{12}$ is prepared and isolated as described in Reuther, 2002. Next, bromination of the carbons alpha in position relative to the 1,3 dicarbonyl groups of the malonate portions of cyclo-[3]-octylmalonate is performed with 3.1 equivalents of bromine (or an alternatively suitable bromination agent, e.g., N-bromosuccinimide). Alternatively, a suitable halogenation (Cl or I) agent can be employed, e.g., N-halosuccinimide). The trobrominated product $C_{33}H_{51}O_{12}Br_3$ is purified by flash chromatography on silica gel. Alternatively, chlorination or iodination of the alpha-carbon positions can be performed in place of bromination. The cyclo-[3]-octylmalonate is thus converted to the suitable cyclopropanation reagent (reaction substrate) by tris-halogenation.

An example of the reaction of this tether with $C_{60}$ is presented here. The reaction procedure is conducted inside of the glovebox. $C_{60}$ powder (100 mg, ~1.4×10$^{-4}$ moles) is stirred vigorously in 5 ml dried tetrahydrofuran (THF) for five minutes. One equivalent of tribrominated cyclo-[3]-octylmalonate (122 mg, ~1.4×10$^{-4}$ moles) is added; the mixture is rapidly stirred for 5 minutes. Next, excess solid KH (50 mg, 1.3×10$^{-3}$ moles) is added while stirring rapidly. Within several seconds, bubbles from the evolution of H$_{2(g)}$ are visible, and within 5 minutes the dark brown color of derivatized fullerene is observed in solution. The reaction mixture can be stirred for as little as 15 minutes; usually it is stirred for 1.5 hours to allow for maximum reaction yield, but this is not required. Then the stirring is halted, the unreacted portion of the fullerenes and KH is allowed to settle, and very dark-brown solution is decanted away. This solution is passed through a 0.45 µm Millipore membrane filter and the THF solvent is removed under vacuum. The product is analyzed by LD-TOF MS (from a sulfur matrix) showing the addition of one tether group per $C_{60}$ (as $C_{60}(C_{33}H_{48}O_{12})$, m/z=1357), with negligible amounts of a two tether groups attached per $C_{60}$ compound formed. This derivative now has solubility in a variety of common polar and non-polar organic solvents. Chromatographic purification can be used to separate the majority e, e, e isomer product from minority amounts of trans-4, trans-4, trans-4 isomer product as described in Reuther 2002.

The tether-derivatized $C_{60}$ species can be converted to the water-soluble species by removing the tether with de-esterification to carboxylic acid or carboxylate salt groups. This is performed by the method of Hirsch (Lamparth, 1994). The ester derivative (100 mg) is dissolved in toluene (15 mL) and vigorously stirred at reflux with excess solid NaH (100 mg) under argon for 2-3 hours. Next, methanol (3 mL) is added with stirring. Vigorous bubbling is observed, followed by precipitation of the sodium carboxylate salt of the $C_{60}$ derivative. Aqueous acidification yields chiefly $C_3$-$C_{60}$[C(COOH)$_2$]$_3$ (with possible minor amounts of other isomer(s) depending on derivatization reaction conditions and any chromatographic purification performed as above). These improvements are valuable as the trisadduct compounds of formula $C_{60}$[C(COOH)$_2$]$_3$ have potential pharmaceutical applications as neuroprotectants (U.S. Pat. No. 6,265,443) based on well-documented antioxidant and radical scavenging properties.

The cyclopropanation reagent of the method of this invention can also be generated in situ by treatment of cyclo-[3]-octylmalonate with halogen-releasing agents such as $CBr_4$, $I_2$, etc. (as described by Camps, 1997; Nierengarten, 1997). This allows for derivatization without prior isolation of the trihalogenated cyclo-[3]-octylmalonate species. The Camps and Nierengarten references are specifically incorporated by reference herein to provide details including useful halogen-releasing agents and esters and acids of in situ generation of cyclopropanation reagents.

The above example with $C_{60}$ is illustrative of the application of the new reaction conditions for attaching a tethered multi-functional cyclopropanation reagent; this reaction is generally applicable other fullerenes classes including: the insoluble M@$C_{60}$ class of M@$C_{2n}$, soluble-as-ions $M_x$@$C_{2n}$ species, insoluble small-bandgap $C_{2n}$ fullerenes including $C_{74}$, insoluble "giant" fullerenes $C_{2n}$ (where n>50), soluble $C_{2n}$, soluble $M_x$@$C_{2n}$, and other endohedral fullerenes, metal-carbon nanoencapsulates and carbon nanotubes. These reactions may be performed with different size tethered cyclopropanation reagents such as cyclo-[n]-octylmalonates with n>3 as well as modified cyclo-species with different length and composition spacers in place of the octyl groups. This can also include tether motifs that link malonates or similar reactive substrate groups with a chemical backbone entirely different from the above cyclo-[n]-alkyl motif.

Radioactive—Metal Containing $M@C_{60}$ and $M_m@C_{2n}$

The disclosed derivatization method works on radioactive-metal containing $M@C_{60}$ and $M_m@C_{2n}$ produced by the following methods:

- arc synthesis with radioactive metal precursor(s) followed by purification, etc.
- neutron activation after manufacture/purification of endohedral species (Cagle, 1999).
- "ion implantation" of radioactive elements into the fullerene cage
- nuclear recoil implantation via activation of interstitially embedded elements in solid fullerene lattices.

The disclosed invention provides an easy and convenient means for derivatizing and solubilizing radioactive-metal containing endohedral fullerenes, including $M@C_{60}$ species, which are normally insoluble. This is particularly important, because with generation techniques of ion implantation and nuclear recoil/neutron activation of interstitials, the starting fullerene can be pure $C_{60}$, so any endohedrals generated will be $M_m@C_{60}$ species. It can also be important to have a fast-acting solubilization reaction, which this invention provides, because the half-lives of some of the desired radioactive nuclei may be relatively short. Solubilization in general, and water solubilization specifically, are required for the radioactive endohedrals to function successfully as radio-pharmaceuticals. A detailed example of the advantages the disclosed invention convey to endohedral fullerene radiopharmaceuticals is below.

This example illustrates how the difference in the solubility between $M@C_{60}$ and empty $C_{60}$ can be combined with the new derivatization method to prepare a carrier free, high specific activity $C_{60}$-based radionuclide carrier that is useful for nuclear medicine is described below.

Holmium oxide, $HO_2O_3$, powder was coated with $C_{60}$ from toluene solution by evaporation in a rotary evaporator to yield holmium oxide particles covered with a thin layer of $C_{60}$. The coated particles were dried under vacuum with a 12-hour temperature ramp starting at room temperature and ending at 250° C. After drying, approximately 100 mg of the coated particles was sealed under He in an aluminum can suitable for insertion into the core of the high flux isotope reactor (HFIR) at Oak Ridge National Laboratory.

The sample was subsequently irradiated with thermal neutrons at a flux $1 \times 10^{14}$ or greater for period of several hours. During neutron activation, $^{165}Ho$ atoms in the holmium oxide absorb neutrons and are converted to $^{166}Ho$, a beta-emitting radioisotope with a half-life of 26 hrs that is suitable for cancer treatments and other nuclear medicine uses. Absorption of a neutron produces a prompt gamma decay, which causes the newly formed $^{166}Ho$ to recoil with range of energies up to a maximum energy of 126 eV. Some of the more energetic recoils free the $^{166}Ho$ from the holmium oxide lattice allowing it to infiltrate into the $C_{60}$ layers. A fraction (1-10%) of these recoiling nuclei then penetrate the $C_{60}$ cages producing $^{166}Ho@C_{60}$ radio-metallofullerene molecules. In addition to the $^{166}Ho@C_{60}$, the nuclear recoil reactions also produce fractured and/or fragmented $C_{60}$ molecules that subsequently polymerize, $^{166}Ho$ atoms that are intercalated into the $C_{60}$ lattice, and hot $^{166}Holmium$ oxide. Insertion of atoms into $C_{60}$ by nuclear recoil has been described (Braun, 1998) while the processes that occur to fullerenes and metallofullerenes during nuclear activation has been thoroughly reviewed by Thrash et. al. (Thrash, 1999).

After removal from the reactor, the sample can was emptied into toluene solution and the holmium oxide particles were thoroughly washed to remove empty $C_{60}$. The washes were repeated until the toluene was clear. The insoluble material containing the holmium oxide, insoluble $^{166}Ho@C_{60}$, and polymerized $C_{60}$ was then subjected to the derivatization reaction with diethylbromomalonate in THF using the procedure outlined previously for $Gd@C_{60}$. The $^{166}Ho@C_{60}$ was derivatized with up to 9-10 ethyl malonates and became soluble in the THF, while the fractured $C_{60}$ polymer and holmium oxide particles remain insoluble. The THF solution was then filtered to yield nearly pure $^{166}Ho@C_{60}(C(COOCH_2CH_3)_2)_x$, $x \cong 1$-10. Some derivatized $C_{60}$ and derivatized $C_{60}$ oligomers (dimers, trimers) may also be present. As noted earlier, 1-3 oxygen atoms as epoxides or other configurations may be present on the derivatized $^{166}Ho@C_{60}$. $^{166}Ho$ ions complexed by THF are also present in the solution. Depending on the activation parameters and the amount of time elapsed since the end of activation, a variable (but which can be calculated) amount of $^{166}Er@C_{60}(C(COOCH_2CH_3)_2)_x$, the decay product of the $^{166}Ho$, will also be present.

The THF is removed by evaporation and the $^{166}Ho@C_{60}(C(COOCH_2CH_3)_2)_x$ carboxylic acid ester is then re-dissolved in toluene. $^{166}Ho$ salts and any reduced $C_{60}$ are not soluble in the non-polar toluene. The sample is then de-esterified using the process previously described producing the water soluble sodium carboxylate salt $^{166}Ho@C_{60}(C(COONa)_2)_x$, which was then dissolved in ultra high purity de-ionized water. The water-soluble sample was then filtered through a $H^+$ loaded ion exchange column to remove excess hydroxide from the de-esterification process and any remaining traces of $^{166}Ho$. The sample, now in the free acid form is ready for further derivatization to produce compounds for nuclear medicine. It could for example be conjugated to monoclonal antibodies or polypeptides to form targeted cancer therapies using standard methods for linking carboxylic acids to proteins and peptides.

A point to note is that the metallofullerenes only encapsulate the radioactive species, thus producing a carrier-free compound with a very high specific activity; i.e., all of the metallofullerenes are radioactive, which is what is required for successful cancer therapies. The second key point is that the new derivatization method allows only the radioactive metallofullerenes to simultaneously derivatized and purified from the other compounds such as $C_{60}$, polymerized $C_{60}$, free $^{166}holmium$, and holmium oxide present in the irradiated sample. Any reactive substrate suitable with the disclosed method could have been used in place of the diethylbromomalonate including reactants containing peptide linkers or even small peptides. The radioisotope is not limited to $^{166}Ho$, but can be any radioisotope capable of recoiling into a fullerene during neutron activation and that forms a toluene insoluble endohedral fullerene suitable for use with the new disclosed derivatization reaction(s).

Applications for the cyclopropanated endohedral metallofullerene radiopharmaceuticals include radiotracers (possibly capable of crossing the blood-brain barrier) for nuclear imaging, therapeutics (with the possibility of targeting via attached functionalities) and as components in fullerene coatings of medical prosthetic devices.

Another pharmaceutical application for endohedral metallofullerenes is use as generators of singlet oxygen (Tagmatarchis, 2001), which can be used therapeutically in vivo to treat disease.

Those of ordinary skill in the art will appreciate that materials and methods other than those specifically described herein can be employed in the practice of this invention without departing from the scope of this invention.

All references cited herein are hereby incorporated by reference in their entirety to the extent that they are not inconsistent with the disclosure herein.

REFERENCES

Akasaka, T.; Kato, T.; Kobayashi, K.; Nagase, S.; Yamamoto, K.; Funasaka, H.; Takahashi, T. (1995)(a). "Exohedral Adducts of La@$C_{82}$," *Nature*, 374, 600-601.

Akasaka, T.; Nagase, S.; Kobayashi, K.; Suzuki, T.; Kato, T.; Kikuchi, K.; Achiba, Y.; Yamamoto, K.; Funasaka, H.; Takahashi, T. (1995)(b). "Synthesis of the First Adducts of the Dimetallofullerenes $La_2$@$C_{80}$ and $Sc_2$@$C_{84}$ by Addition of a Disilirane," *Angew. Chem. Intl. Ed. Engl.*, 34, 2139-2141.

Akasaka, T.; Nagase, S.; Kobayashi, K.; Suzuki, T.; Kato, T.; Yamamoto, K.; Funasaka, H.; Takahashi, T. (1995)(c). "Exohedral Derivatization of an Endohedral Metallofullerene Gd@$C_{82}$," *Chem. Comm.*, 1343-1344.

Balch, A. L.; Olmstead, M. M. (1998). "Reactions of Transition Metal Complexes with Fullerenes ($C_{60}$, $C_{70}$, etc.) and Related Materials" *Chem. Rev.* 98, 2123-2166.

Beer, F.; Gügel, A.; Martin, K.; Räder, J.; Müllen, K. (1997). "High-Yield Reactive Extraction of Giant Fullerenes from Soot," *J. Mater. Chem.*, 7, 1327-1330.

Bethune, D. S.; Johnson, R. D.; Salem, J. R.; de Vries, M. S.; Yannoni, C. S. (1993) "Atoms in carbon cages: the structure and properties of endohedral fullerenes", *Nature* 366, 123-128.

Beulen, M. W. J.; Echegoyen, L.; Rivera, J. A.; Herranz, M. A.; Martin-Domenech, A.; Martin, N. (2000). "Adduct Removal from Methanofullerenes via Reductive Electrochemistry," *Chem. Comm.*, 917-918.

Bingel, C. (1993). "Cyclopropanierung von Fullerenen," *Chem. Ber.*, 126, 1957-1959.

Bingel, C.; Schiffer, H. (1995). "Biscyclopropanation of $C_{70}$," *Liebigs Ann.*, 1551-1553.

Bingel, C. (1998). "Fullerene Derivatives, Methods of Preparing Them, and Their Use," U.S. Pat. No. 5,739,376.

Braun, T.; Rausch, H. (1998). "Radioactive endohedral metallofullerene formed by prompt gamma-generated nuclear recoil implosion", *Chem. Phys. Lett.* 288, 179-182.

Brettreich, M.; Hirsch, A. (1998). "A Highly Water-Soluble Dendro[60]fullerene," *Tet. Lett.*, 39, 2731-2734.

Cagle, W. D.; Thrash, T. P.; Alford, J. M.; Chibante, L. P. F.; Ehrhardt, G. J.; Wilson, L. J. (1996). "Synthesis, Characterization, and Neutron Activation of Holmium Fullerenes", *J. Am. Chem. Soc.* 118, 8043-8047.

Cagle, D. W.; Kennel, S. J.; Mirzadeh, S.; Alford, J. M.; Wilson, L. J. (1999) "In vivo studies of fullerene-based materials using endohedral metallofullerene radiotracers", *Proc. Natl. Acad. Sci. USA* 96, 5182-5187.

Camps, X.; Hirsch, A. (1997). "Efficient Cyclopropanation of $C_{60}$ Starting from Malonates," *J. Chem. Soc. Perkin Trans.* 1, 1595-1596.

Caravan, P.; Elllison, J. J.; McMurry, T. J.; Lauffer, R. B. (1999). "Gadolinium(III) Chelates as MRI Contrast Agents: Structure, Dynamics, and Applications," *Chem. Rev.*, 99, 2293-2352.

Cheng, F.; Yang, X.; Zhu, H.; Song, Y. (2000). "Synthesis and Optical Properties of Tetraethyl Methano[60]fullerenediphosphonate," *Tet. Lett.*, 41, 3947-3950.

Cross, R. J.; Jiménez-Vazquez, H. A.; Lu, Q.; Saunders, M.; Schuster, D. I.; Wilson, S. R.; Zhao, H. (1996). "Differentiation of Isomers Resulting from Bisaddition to $C_{60}$ Using $^3$He NMR Spectroscopy," *J. Am. Chem. Soc.*, 118, 11454-11459.

Diederich, F.; Ettl, R.; Rubin, Y.; Whetten, R. L.; Beck, R.; Alvarez, M.; Anz, S.; Sensharma, D.; Wudl, F.; Khemani, K. C.; Koch, A. (1991). "The Higher Fullerenes: Isolation and Characterization of $C_{76}$, $C_{84}$, $C_{90}$, $C_{94}$, and $C_{70}O$, an Oxide of $D_{5h}$-$C_{70}$" *Science*, 252, 548-551.

Diederich, F.; Kessinger, R. (1999). "Templated Regioselective and Stereoselective Synthesis in Fullerene Chemistry," *Acc. Chem. Res.*, 32, 537-545.

Diener, M. D.; Alford, J. M. (1998) "Isolation and Properties of Small-Bandgap Fullerenes," *Nature* 393, 668-671.

Dietel, E.; Hirsch, A.; Pietzak, B.; Waiblinger, M.; Lips, K.; Weidinger, A.; Gruss, A.; Dinse, K. P. (1999). "Atomic Nitrogen Encapsulated in Fullerenes: Effects of Cage Variations," *J. Am. Chem. Soc.*, 121, 2432-2437.

Dugan, L. L.; Lovett, E.; Cuddihy, S.; Ma, B.-W.; Lin, T.-S.; Choi, D. W. (2000). "Carboxyfullerenes as Neuroprotective Antioxidants," in *Fullerenes: Chemistry, Physics, and Technology*, Kadish, K. M. and Ruoff, R. S. eds., John Wiley & Sons, New York, 467-479.

Hinokuma, K.; Ata, M. (2001)(a). "Fullerene Proton Conductors," *Chem. Phys. Lett.*, 341, 442-446.

Hinokuma, K.; Ata, M. (2001) (b). "Proton Conductor and Method for Manufacturing Thereof, and Fuel Cell," European Patent Application Number EP 1 071 149 A2.

Hirsch, A. (1994)(a). *The Chemistry of the Fullerenes*, Georg Thieme Verlag Stuttgart, New York.

Hirsch, A.; Lamparth, I.; Karfunkel, H. R. (1994)(b). "Fullerene Chemistry in Three Dimensions: Isolation of Seven Regioisomeric Bisadducts and Chiral Trisadducts of $C_{60}$ and Di(ethoxycarbonyl)methylene," Angew. Chem. Int. Ed., 33, 437-438.

Inoue, T.; Kubozono, Y.; Kashino, S.; Takabayashi, Y.; Fujitaka, K.; Hida, M.; Inoue, M.; Kanbara, T.; Emura, S.; Uruga, T. (2000). "Electronic Structure of Eu@$C_{60}$ Studied by XANES and UV-VIS Absorption Spectra," *Chem. Phys. Lett.*, 316, 381-386.

Jung, M. E. (1991). "Stabilized Nucleophiles with Electron Deficient Alkenes and Alkynes," in *Comprehensive Organic Synthesis: Selectivity, Strategy, & Efficiency in Modern Organic Chemistry*, Trost, B. M.; Fleming, I. eds., Pergamon Press, Oxford, volume 4, 1-67.

Kato, T.; Akasaka, T.; Kobayashi, K.; Nagase, S.; Kikuchi, K.; Achiba, Y.; Suzuki, T.; Yamamoto, K. (1997). "Chemical Reactivities of Endohedral Metallofullerenes," *J. Phys. Chem. Solids*, 58, 1779-1783.

Kessinger, R.; Gómez-López, M.; Boudon, C.; Gisselbretch, J.-P.; Gross, M.; Echegoyen, L.; Diederich, F. (1998). "Walk On the Sphere: Electrochemically Induced Isomerization of $C_{60}$ Bis-adducts by Migration of Di(alkoxycarbonyl)methano Bridges," *J. Am. Chem. Soc.*, 120, 8545-8546.

Khong, A.; Cross, R. J.; Saunders, M. (2000). "From $^3$He@$C_{60}$ to $^3$H@$C_{60}$: Hot-Atom Incorporation of Tritium in $C_{60}$," *J. Am. Chem. Soc.*, 104, 3940-3943.

Klos, H.; Rystau, I.; Schütz, W.; Gotschy, B.; Skiebe, A.; Hirsch, A. (1994). "Doping of $C_{60}$ with Tertiary Amines: TDAE, DBU, DBN. A Comparative Study," *Chem. Phys. Lett.*, 224, 333-337.

Krätschmer, W.; Lamb, L. D.; Fostiropoulos, K.; Huffman, D. R. (1990) "Solid $C_{60}$: A New Form of Carbon", *Nature* 347, 354-358.

Kubozono, Y.; Ohta, T.; Hayashibara, T.; Maeda, H.; Ishida, H.; Kashino, S.; Oshima, K.; Yamazaki, H.; Ukita, S.; Sogabe, T. (1995). "Preparation and Extraction of Ca@$C_{60}$," *Chem. Lett.*, 457-458.

Kubozono, Y.; Noto, T.; Ohta, T.; Maeda, H.; Kashino, S.; Emura, S.; Ukita, S.; Sogabe, T. (1996)(a). "Extractions of Ca@$C_{60}$ and Sr@$C_{60}$ with Aniline," Chem. Lett., 453-454.

Kubozono, Y.; Maeda, H.; Takabayashi, Y.; Hiraoka, K.; Nakai, T.; Kashino, S.; Emura, S.; Ukita, S.; Sogabe, T. (1996)(b). "Extractions of Y@$C_{60}$, Ba@$C_{60}$, La@$C_{60}$, Ce@$C_{60}$, Pr@$C_{60}$, Nd@$C_{60}$, and Gd@$C_{60}$ with Aniline," J. Am. Chem. Soc., 118, 6998-6999.

Lamparth, I.; Hirsch, A. (1994). "Water-Soluble Malonic Acid Derivatives of $C_{60}$ with a Defined Three-Dimensional Structure," Chem. Comm., 1727-1728.

Lamparth, I.; Schick, G.; Hirsch, A. (1997). "Side-Chain Modification of $C_{60}$ via Activation of the Easily Accesible Fulleromalonic Acid $C_{61}(COOH)_2$," Liebigs Ann./Recueil, 253-258.

Liu, S.; Sun, S. (2000) "Recent progress in the studies of endohedral metallofullerenes", J. Organomet. Chem. 599, 74-86.

McHenry, M. E.; Subramoney, S. (2000). "Synthesis, Structure, and Properties of Carbon Encapsulated Metal Nanoparticles," in Fullerenes: Chemistry, Physics, and Technology, Kadish, K. M. and Ruoff, R. S. eds., John Wiley & Sons, New York, 839-885.

Mikawa, M.; Kato, H.; Okumura, M.; Narazaki, M.; Kanazawa, Y.; Miwa, N.; Shinohara, H. (2001). "Paramagnetic Water-Soluble Metallofullerenes Having the Highest Relaxivity for MRI Contrast Agents," Bioconj. Chem., 12, 510-514.

Moonen, N. N. P.; Thilgen, C.; Echegoyen, L.; Diederich, F. (2000). "The Chemical Retro-Bingel Reaction: Selective Removal of Bis(alkoxycarbonyl)methano addends from $C_{60}$ and $C_{70}$ with Amalgamated Magnesium," Chem. Comm., 335-336.

Nagase, S.; Kobayashi, K.; Akasaka, T. (1996) "Endohedral Metallofullerenes: New Spherical Cage Molecules with Interesting Properties", Bull. Chem. Soc. Jpn. 69, 2131-2142.

Nagase, S.; Kobayashi, K.; Akasaka, T., Wakahara, T. (2000) "Endohedral Metallofullerenes: Theory, Electrochemistry, and Chemical Reactions," in Fullerenes: Chemistry, Physics. and Technology, Kadish, K. M. and Ruoff, R. S. eds., John Wiley & Sons, New York, 395-436.

Nierengarten, J.-F.; Nicoud, J.-F. (1997). "Cyclopropanation of $C_{60}$ with Malonic Acid Mono-Esters," Tet. Lett., 38, 7737-7740.

Nuretdinov, I. A.; Gubskaya, V. P.; Berezhnaya, L. Sh.; Il'yasov, A. V.; Azancheev, N. M. (2000). "Synthesis of Phosphorylated Methanofullerenes," Russ. Chem. Bull., 49, 2048-2050.

Okada, S.; Saito, S. (2000) "Stable Polymers of $C_{74}$ and $C_{78}$ Fullerenes," Chem. Phys. Lett., 321, 156-162.

Ogawa, T.; Sugai, T.; Shinohara, S. (2000). "Isolation and Characterization of Er@$C_{60}$," J. Am. Chem. Soc., 122, 3538-3539.

Parker, D. H.; Wurz, P.; Chatterjee, K.; Lykke, K. R.; Hunt, J. E.; Pellin, M. J.; Hemminger, J. C.; Gruen, D. M.; Stock, L. M. (1991). "High-Yield Synthesis, Separation, and Mass-Spectrometric Characterization of Fullerenes $C_{60}$ to $C_{266}$," J. Am. Chem. Soc., 113, 7499-7503.

Pellicciari, R.; Natalini, B.; Amori, L.; Marinozzi, M.; Seraglia, R. (2000). "Synthesis of Methano[60]fullerenephosphonic- and Methano[60]fullerenediphosphonic Acids," Synlett, 1816-1818.

Reed, C. A.; Bolskar, R. D. (2000) "Discrete Fulleride Anions and Fullerenium Cations", Chem. Rev. 100, 1075-1120.

Rapenne, G.; Crassous, J.; Collet, A.; Echegoyen, L.; Diederich, F. (1999). "Regioselective one-step synthesis of trans-3, trans-3, trans-3 and e, e, e [60]fullerene tris-adducts by a $C_3$-symmetrical cyclotriveratrylene tether," J. Chem. Soc. Chem. Commun. 1121-1122.

Reuther, U.; Brandmüller, T.; Donaubauer, W.; Hampel, F.; Hirsch, A. (2002). "A Highly Regioselective Approach to Multiple Adducts of $C_{60}$ Governed by Strain Minimization of Macrocyclic Malonate Addends," Chem. Eur. J., 8, 2261-2273.

Richardson, C. F.; Schuster, D. I.; Wilson, S. R. (2000). "Synthesis and Characterization of Water-Soluble Amino Fullerene Derivatives," Org. Lett., 2, 1011-1014.

Ruoff, R. S.; Tse, D. S.; Malhotra, R.; Lorents, D. C. (1993) "Solubility of $C_{60}$ in a Variety of Solvents", J. Phys. Chem. 97, 3379-3383.

Skiebe, A.; Hirsch, A.; Klos, H.; Gotschy, B. (1994). "[DBU] $C_{60}$. Spin Pairing in a Fullerene Salt," Chem. Phys. Lett., 220, 138-140.

Shinohara, H. (2000). "Endohedral Metallofullerenes: Production, Separation, and Structural Properties," in Fullerenes: Chemistry, Physics, and Technology, Kadish, K. M. and Ruoff, R. S. eds., John Wiley & Sons, New York, 357-393.

Shinohara, H. (2000). "Endohedral Metallofullerenes," Rep. Prog. Phys., 63, 843-892.

Stevenson, S.; Rice, G.; Glass, T.; Harich, K.; Cromer, F.; Jordan, M. R.; Craft, J.; Hadju, E.; Bible, R.; Olmstead, M. M.; Maitra, K.; Fisher, A. J.; Balch, A. L.; Dorn, H. C. (1999) "Small-bandgap endohedral metallofullerenes in high yield and purity", Nature 401, 55-57.

Sun, D.; Huang, H.; Yang, S.; Liu, Z.; Liu, S. (1999) "A Simple Method for the Selective Enrichment of Endohedral Metallofullerenes", Chem. Mater. 11, 374-377.

Suzuki, T.; Maruyama, Y.; Kato, T.; Akasaka, T.; Kobayashi, K.; Nagase, S.; Yamamoto, K.; Funasaka, H.; Takahashi, T. (1995). "Chemical Reactivity of a Metallofullerene: EPR Study of Diphenylmethano-La@$C_{82}$ Radicals," J. Am. Chem. Soc., 117, 9606-9607.

Tagmatarchis, N.; Kato, H.; Shinohara, H. (2001). "Novel Singlet Oxygen Generators: The Nature and the Number of Trapped Metal Atoms in Endohedral Metallofullerenes M@$C_{82}$ (M=Dy, Gd, La) and $Dy_2$@$C_2$, (2n=84-94)," Phys. Chem. Chem. Phys., 3, 3200-3202.

Taylor, R.; Barrow, M. P.; Drewello, T. (1998). "$C_{60}$ Degrades to $C_{120}O$," Chem. Comm., 2497-2498.

We claim

1. A method for derivatizing one or more fullerenes comprising the steps of:
   a. providing the one or more fullerenes as a solid; and
   b. contacting the fullerene solid with a suitable base, and a cyclopropanation reagent in the presence of an at least moderately polar aprotic solvent in which the one or more fullerenes to be derivatized are insoluble or substantially insoluble, wherein the cyclopropanation reagent has the formula:

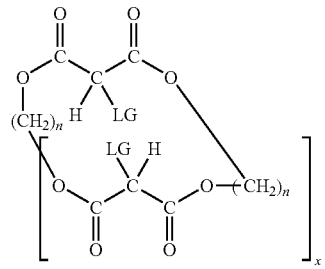

where LG is a leaving group and n is an integer ranging from 2 to 20 and x is an integer ranging from 1-10.

2. The method of claim 1 wherein n is 6-10.
3. The method of claim 1 wherein x is 1-5.
4. The method of claim 1 wherein LG is —Cl, —Br, or —I.

5. A method for derivatizing fullerenes comprising the steps of:
provided one or more fullerenes as a solid; and
contacting the fullerene solid with a solution comprising an at least moderately polar aprotic solvent in which the one or more fullerenes are soluble at a level of about 0.001 mg/mL or less, a suitable base, and a cyclopropanation reagent, wherein the one or more fullerenes is an empty small bandgap fullerene.

6. A method for derivatizing fullerenes comprising the steps of:
providing one or more fullerenes as a solid; and
contacting the fullerene solid with a solution comprising an at least moderately polar aprotic solvent in which the one or more fullerenes are soluble at a level of about 0.001 mg/mL or less, a suitable base, and a cyclopropanation reagent
wherein the fullerene is an endohedral M@C60 class fullerene and M is an element selected from the group consisting of lanthanide metals, actinide metals, transition metals, alkali metals, and alkaline earth metals.

7. The method of claim 6 wherein M is a lanthanide metal.

8. The method of claim 7 wherein M is Gd.

9. The method of claim 6 wherein the fullerene is an endohedral M@C60 class fullerene and M is a radioactive element.

10. The method of claim 6 wherein the at least moderately polar aprotic solvent is selected from the group consisting of: aliphatic ethers, aryl ethers, cyclic ethers, halogenated alkanes, halogenated benzenes, dialkylsulfoxides and miscible combinations thereof.

11. The method of claim 10 wherein the at least moderately polar aprotic solvent is selected from the group consisting of dichloromethane, tetrachloroethane, ortho-dichlorobenzene, halobenzenes and miscible combinations thereof.

12. A method for derivatizing fullerenes comprising the steps of:
providing one or more fullerenes as a solid; and
contacting the fullerene solid with a solution comprising an at least moderately polar aprotic solvent in which the one or more fullerenes are soluble at a level of about 0.001 mg/mL or less, a suitable base, and a cyclopropanation reagent, wherein the solvent is tetrahydrofuran, 1,4-dioxane or dimethoxyethane.

13. The method of claim 12 wherein a mixture of fullerenes is derivatized.

14. The method of claim 12 wherein the one or more fullerenes is a giant fullerene.

15. The method of claim 12 wherein the one or more fullerenes is a metal-carbon nanoencapsulate.

16. The method of claim 12 wherein the step of contacting is carried out in an air-free environment.

17. The method of claim 12 wherein an excess of cyclopropanation reagent and base are added.

18. The method of claim 12 wherein the solvent is tetrahydrofuran.

19. The method of claim 6 wherein the solid fullerene is provided in powdered form.

20. The method of claim 6 conducted at ambient temperature.

21. A method for derivatizing fullerenes comprising the steps of:
providing one or more fullerenes as a solid; and
contacting the fullerene solid with a solution comprising an at least moderately polar aprotic solvent in which the one or more fullerenes are soluble at a level of about 0.001 mg/mL or less, a suitable base, and a cyclopropanation reagent, wherein the one or more fullerenes are insoluble fullerenes, wherein the cyclopropanation reagent has two or more cyclopropanation reaction groups cojoined in one molecule.

22. The method of claim 21 wherein the two or more cyclopropanation groups of the same cyclopropanation reagent molecule react with more than one fullerene molecule.

23. A method for derivatizing fullerenes comprising the steps of:
providing one or more fullerenes as a solid; and
contacting the fullerene solid with a solution comprising an at least moderately polar aprotic solvent in which the one or more fullerenes are soluble at a level of about 0.001 mg/mL or less, a suitable base, and a cyclopropanation reagent
wherein the cyclopropanation reagent is a cyclo-[n]-alkylmalonate which is substituted with a leaving group at the alpha carbon of one or more malonate moieties in the reagent.

24. The method of claim 23 wherein the cyclopropanation reagent is a cyclo-[n]-octylmalonate which is substituted with a leaving group at the alpha carbon of one or more malonate moieties in the reagent.

25. The method of claim 23 wherein the at least moderately polar aprotic solvent is selected from the group consisting of aliphatic ethers, aryl ethers, cyclic ethers, halogenated alkanes, halogenated aryls, dimethylsulfoxide and miscible combinations thereof.

26. The method of claim 23 wherein the one or more fullerenes are selected from the group consisting of endohedral metallofullerenes, empty C2n small bandgap fullerenes, giant fullerenes, metal-carbon nanoencapsulates and carbon nanotubes.

27. The method of claim 6 wherein the at least moderately polar solvent is dichloromethane or a halogenated benzene.

28. The method of claim 12 wherein the one or more fullerenes are selected from the group consisting of endohedral fullerenes, endohedral metallofullerenes, empty C2n small bandgap fullerenes, giant fullerenes, metal-carbon nanoencapsulates and carbon nanotubes.

29. A method for purification of one or more fullerenes from a mixture which comprises the one or more fullerenes to be purified and non-fullerenic carbonaceous material, which method comprises the steps of:
providing the mixture comprising the one or more fullerenes as a solid, reacting the mixture comprising the one or more fullerenes with a suitable base, and a cyclopropanation reagent in an at least moderately polar aprotic solvent in which the one or more fullerenes to be purified are soluble at a level of about 0.001 mg/mL or less until the one or more fullerenes are derivatized and are soluble in the moderately polar aprotic solvent:
separating the one or more solublized derivatized fullerenes from any non-soluble fullerenes, non-soluble non-fullerenic carbonaceous material or both; and
treating the one or more separated solubilized derivatized fullerenes to remove the groups added by reaction with the cyclopropanation reagent to regenerate the one or more non-derivatized fullerenes, wherein the one or more fullerenes to be purified are insoluble fullerenes, wherein the insoluble fullerenes are selected from an empty small bandgap fullerene, a giant fullerene, a metal-carbon nanoencapsulate, an endohedral M@C60 class fullerene where M is an element selected from the group consisting of lanthanide metals, actinide metals, transition metals, alkali metals, and alkaline earth metals.

30. The method of claim 29 wherein the at least moderately polar aprotic solvent is selected from the group consisting of aliphatic ethers, aryl ethers, cyclic ethers, dialkylsulfoxides and miscible combinations thereof.

31. The method of claim 29 wherein the at least moderately polar aprotic solvent is a non-halogenated polar solvent.

32. The method of claim 29 wherein the cyclopropanation reagent has the formula:

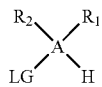

where A is a C or Si atom;
LG is a leaving group; and
$R_1$ and $R_2$ are independently selected from the group consisting of alkyl, alkenyl, alkynyl, or aryl groups optionally substituted with one or more OH, COOH, COOAr, COOCH$_2$Ar, CONHCH$_2$Ar, CONHAr, halogen, CONH$_2$, COCH$_2$Ar, COAr, CO ($C_1$-$C_6$)-alkyl or CHO substituents, —COOR$_3$ groups, —O—CO—R$_3$ groups, —COR$_3$ groups, —CO—NR$_3$R$_4$ groups, —O—CO—NR$_3$R$_4$ groups, —CN, —P(O)(OR$_3$)(OR$_4$) groups, and —SO$_2$R$_3$ groups where $R_3$ and $R_4$ are independently selected from hydrogen, or an alkyl group, alkenyl group, alkynyl group or aryl group any of which may be optionally substituted with one or more OH, COOH, COOAr, COOCH$_2$Ar, CONHCH$_2$Ar, CONHAr, halogen, CONH$_2$, COCH$_2$Ar, COAr, CO ($C_1$-$C_6$)-alkyl or CHO or —NR$_5$R$_6$, where $R_5$ and $R_6$, independently, are hydrogen, an aryl group, an alkyl group, or an alkenyl group, and wherein one or more non-neighboring CH$_2$ moieties in $R_3$ or $R_4$, can be replaced with an O or S atom and wherein one or both of $R_1$ and $R_2$ are substituted with at least one substituent that stabilizes a negative charge inductively or by electron delocalization to render the H bonded to A acidic and $R_1$ and $R_2$ are optionally-substituted with-one or more -AHLG-.

33. The method of claim 12 wherein the one or more fullerenes are selected from an empty small bandgap fullerene, a giant fullerene, a metal-carbon nanoencapsulate, an endohedral M@C60 class fullerene where M is an element selected from the group consisting of lanthanide metals, actinide metals, transition metals, alkali metals, and alkaline earth metals.

34. The method of claim 12 wherein the one or more fullerenes are selected from an empty small bandgap fullerene, or an endohedral M@C60 class fullerene where M is an element selected from the group consisting of lanthanide metals, actinide metals, transition metals, alkali metals, and alkaline earth metals.

35. The method of claim 5 wherein the solvent is tetrahydrofuran, 1,4-dioxane or dimethoxyethane.

* * * * *